United States Patent
Kellerman et al.

(10) Patent No.: US 9,394,314 B2
(45) Date of Patent: *Jul. 19, 2016

(54) 8'-HYDROXY-DIHYDROERGOTAMINE COMPOUNDS AND COMPOSITIONS

(71) Applicant: MAP PHARMACEUTICALS, INC., Mountain View, CA (US)

(72) Inventors: Donald J. Kellerman, Mountain View, CA (US); Thomas Armer, Mountain View, CA (US); Jian Zhang, Mountain View, CA (US)

(73) Assignee: MAP Pharmaceuticals, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/134,100

(22) Filed: Dec. 19, 2013

(65) Prior Publication Data

US 2014/0179704 A1    Jun. 26, 2014

Related U.S. Application Data

(60) Provisional application No. 61/745,104, filed on Dec. 21, 2012.

(51) Int. Cl.
*C07D 498/04*    (2006.01)

(52) U.S. Cl.
CPC ............................ *C07D 498/04* (2013.01)

(58) Field of Classification Search
CPC ...................................... C07D 498/04
USPC .......................................... 514/250; 544/346
See application file for complete search history.

(56) References Cited

U.S. PATENT DOCUMENTS

| | | | |
|---|---|---|---|
| 4,650,810 A | 3/1987 | Bays et al. | |
| 4,914,125 A | 4/1990 | Baldinger et al. | |
| 4,916,125 A | 4/1990 | Herrling et al. | |
| 4,916,132 A | 4/1990 | Seibel | |
| 4,994,483 A | 2/1991 | Oxford et al. | |
| 5,021,428 A | 6/1991 | Carr et al. | |
| 5,069,911 A | 12/1991 | Ziiger | |
| 5,192,528 A | 3/1993 | Radhakrishnan et al. | |
| 5,200,413 A | 4/1993 | King et al. | |
| 5,242,949 A | 9/1993 | Goldberg et al. | |
| 5,248,684 A | 9/1993 | Suzuki et al. | |
| 5,273,759 A | 12/1993 | Simmons | |
| 5,317,103 A | 5/1994 | Baker et al. | |
| 5,364,863 A | 11/1994 | Cohen et al. | |
| 5,399,574 A | 3/1995 | Robertson et al. | |
| 5,434,154 A | 7/1995 | Smith et al. | |
| 5,441,969 A | 8/1995 | Axelsson et al. | |
| 5,464,864 A | 11/1995 | King et al. | |
| 5,466,699 A | 11/1995 | Robertson et al. | |
| 5,468,768 A | 11/1995 | Cipollina et al. | |
| 5,491,148 A | 2/1996 | Berger et al. | |
| 6,043,244 A | 3/2000 | Caruso | |
| 6,264,981 B1 | 7/2001 | Zhang et al. | |
| 6,495,535 B1 | 12/2002 | Plachetka et al. | |
| 6,685,951 B2 | 2/2004 | Cutler | |
| 7,060,694 B2 | 6/2006 | Plachetka et al. | |
| 7,994,197 B2 | 8/2011 | Cook et al. | |
| 8,119,639 B2 | 2/2012 | Cook et al. | |
| 8,148,377 B2 | 4/2012 | Cook et al. | |
| 2003/0008005 A1 | 1/2003 | Cutler | |
| 2003/0017175 A1 | 1/2003 | Cutler | |
| 2003/0022910 A1 | 1/2003 | Cutler | |
| 2003/0114476 A1 | 6/2003 | Plachetka et al. | |
| 2003/0181462 A1 | 9/2003 | Doods et al. | |
| 2004/0191178 A1 | 9/2004 | Cutler | |
| 2006/0014774 A1 | 1/2006 | Flieger et al. | |
| 2006/0147389 A1 | 7/2006 | Staniforth et al. | |
| 2006/0240043 A1 | 10/2006 | Meyerson et al. | |
| 2007/0065463 A1 | 3/2007 | Aung-Din | |
| 2007/0202054 A1 | 8/2007 | Pipkin et al. | |
| 2009/0232898 A1 | 9/2009 | Pettersson et al. | |
| 2010/0029665 A1 | 2/2010 | Meyerson et al. | |
| 2010/0081663 A1 | 4/2010 | Cook et al. | |
| 2010/0267676 A1 | 10/2010 | Xu et al. | |
| 2010/0284940 A1 | 11/2010 | Cook et al. | |
| 2010/0288275 A1 | 11/2010 | Djupesland et al. | |
| 2011/0053913 A1 | 3/2011 | Jhamandas et al. | |
| 2011/0118189 A1 | 5/2011 | Farr et al. | |
| 2011/0269742 A1 | 11/2011 | Cogan et al. | |
| 2012/0329806 A1* | 12/2012 | Cook et al. | 514/250 |

FOREIGN PATENT DOCUMENTS

| | | | |
|---|---|---|---|
| DE | 27 37 132 A1 | 2/1978 | |
| DE | 30 18 550 A1 | 12/1980 | |
| EP | 1 242 013 B1 | 5/2010 | |
| EP | 1242013 B1 | 5/2010 | |

(Continued)

OTHER PUBLICATIONS

Diener, Hans Christoph. A Review of Current Treatments for Migraine, Eur Neurol 1994, 34(2):18-25.

Humbert et al. (Sep. 1996). "Human pharmacokinetics of dihydroergotamine administered by nasal spray," Clinical Pharmacology and Therapeutics 60(3): 265-275.

Johnson, K.W. et al. (1998). "Serotonin in Migraine: Theories, Animal Models and Emerging Therapies," vol. 51 in Progress in Drug Research, Jucker, E ed., Birkhäuser Verlag: Basel, Germany, pp. 221-244.

Lipton, R.B. (1997). "Ergotamine Tartrate and Dihydroergotamine Mesylate: Safety Profiles," Headache 37(1): S33-S41.

Mathew, N. T. (Jan. 1997). "Dosing and Administration of Ergotamine Tartrate and Dihydroergotamine," Headache 37(1):526-532.

(Continued)

*Primary Examiner* — Kathrien Cruz
(74) *Attorney, Agent, or Firm* — Barbara C. Potts

(57) ABSTRACT

8'-Hydroxy-Dihydroergotamine (8'-OH DHE) medicinal compounds, compositions, and dosage forms containing such compositions are provided. Also provided herein are methods of treatment, prevention, or amelioration of migraine disorders using the compounds, compositions, dosage forms and administration techniques disclosed herein.

11 Claims, 1 Drawing Sheet

(56) References Cited

FOREIGN PATENT DOCUMENTS

| EP | 2 258 368 A2 | 12/2010 |
|---|---|---|
| EP | 2258368 A2 | 12/2010 |
| FR | 2837708 | 3/2003 |
| SE | 437 766 B | 3/1985 |
| WO | WO-91/11496 A1 | 8/1991 |
| WO | WO-93/11747 A1 | 6/1993 |
| WO | WO-94/22445 A2 | 10/1994 |
| WO | WO-95/21688 A1 | 8/1995 |
| WO | WO-98/13136 A1 | 4/1998 |
| WO | WO-99/66903 A2 | 12/1999 |
| WO | 0006121 | 2/2000 |
| WO | WO-02/06675 A2 | 1/2002 |
| WO | WO-02/19213 | 3/2002 |
| WO | WO-02/019213 | 3/2002 |
| WO | WO-02/32462 A1 | 4/2002 |
| WO | WO-2005/025506 A2 | 3/2005 |
| WO | WO-2006/103407 | 10/2006 |
| WO | WO-02/006675 A3 | 3/2012 |

OTHER PUBLICATIONS

Saper, J.R. et al. (Nov. 2006). "Pharmacology of Dihydroergotamine and Evidence for Efficacy and Safety in Migraine," Headache 46(4): S171-S181.
Schran, H.F. et al. (Jul. 1, 1983) "The Pharmacokinetics and Bioavailability of Subcutaneously Administered Dihydroergotamine, Heparin and the Dihydroergotamine-Heparin Combination," Thrombosis Research 31(1): 51-67.
U.S. Appl. No. 11/717,276, filed Mar. 13, 2007.
U.S. Appl. No. 12/548,304, filed Aug. 26, 2009.
U.S. Appl. No. 12/584,395, filed Sep. 3, 2009.
U.S. Appl. No. 12/592,287, filed Nov. 19, 2009.
U.S. Appl. No. 12/823,981, filed Jun. 25, 2010.
Hanoun, N. et al, Dihydroergotamine and Its Metabolite, 8'-hydroxy-dihydroergo-tamine, as 5-HT1A Receptor Agonists in the Rat Brian, British Journal of Pharmacology, 2003, 424-434, 139.
International Search Report and the Written Opinion of the International Search Authority or the Declaration mailed May 6, 2014, for PCT Application No. PCT/US2013/76422 filed Dec. 19, 2013, 10 pages.
Response to Office Action filed Oct. 16, 2012, for U.S. Appl. No. 11/717,276, filed Mar. 13, 2007, 12 pages.
Final Office Action mailed Jan. 24, 2013, for U.S. Appl. No. 11/717,276, filed Mar. 13, 2007, 12 pages.
Non-final Office Action mailed Apr. 17, 2012, for U.S. Appl. No. 12/823,981, filed Jun. 25, 2010, 20 pages.
Response to Office Action filed Oct. 17, 2012, for U.S. Appl. No. 12/823,981, filed Jun. 25, 2010, 23 pages.
Final Office Action mailed Nov. 27, 2012, for U.S. Appl. No. 12/823,981, filed Jun. 25, 2010, and Notice of Appeal filed on May 15, 2013, 25 pages.
RCE & Amendment filed Oct. 5, 2012, for U.S. Appl. No. 12/592,287, filed Nov. 19, 2009, 13 pages.
Non-final Office Action mailed Apr. 22, 2013, for U.S. Appl. No. 13/406,391, filed Feb. 27, 2012, 41 pages.
Response to Office Action filed Feb. 4, 2013, and Terminal Disclaimers filed Feb. 11, 2013, for U.S. Appl. No. 13/406,391, filed Feb. 27, 2012, 35 pages.
Non-final Office Action mailed Aug. 2, 2012, for U.S. Appl. No. 13/406,391, filed Feb. 27, 2012, 29 pages.
Mathew, N. T. (Jan. 1997). "Dosing and Administration of Ergotamine Tartrate and Dihydroergotamine," Headache 37(1):S26-S32.
RCE & Amendment filed Apr. 23, 2013, for U.S. Appl. No. 11/717,276, filed Mar. 13, 2007, 15 pages.
RCE & Amendment filed Oct. 5, 2012, for U.S. Appl. No. 12/548,304, filed Aug. 26, 2009, 18 pages.
Anonymous. (2000). "The Headaches," Olesen, J. et al. eds., 2nd edition. Lippincott Williams & Wilkins, Philadelphia PA, 10 pages. (Table of Contents Only).

Anonymous. (2004). "Migraine" Part 1 in The International Classification of Headache Disorders 2nd Edition, Cephalalgia 24(Suppl 1) 9-160. (Table of Contents Only).
Bigal, M.E. et al. (Jul. 25, 2006). "Age-Dependent Prevalence and Clinical Features of Migraine." Neurology 67 (2):246-251.
Crawford, et al. (Mar. 2009). "Menstrual Migraine in Adolescents," Headache Mar. 2009, 49(3), pp. 341-347, Epub Feb. 11, 2009.
Lipton, R.B. et al. (Jun. 1993). "Migraine in the United States: A Review of Epidemiology and Health Care Use," Neurology 43(6)(Suppl 3):S6-S10.
Rasmussen, B.K. et al. (Aug. 1992). "Migraine with Aura and Migraine without Aura: An Epidemiological Study," Cephalalgia 12(4):221-228.
Steiner, T.J. et al. (2003). "The Prevalence and Disability Burden of Adult Migraine in England and Their Relationships to Age, Gender and Ethnicity," Cephalalgia 23(7):519-527.
Diener, Hans Christoph. A Review of Current Treatments for Migraine, Eur Neurol 1994, 34(2): 18-25.
Jung, J. et al. (2001). "Particle Design Using Supercritical Fluids: Literature and Patent Survey," J. of Supercritical Fluids 20:179-219.
Klapper, J.A. et al. (Jan. 1992). "Clinical Experience With Patient Administered Subcutaneous Dihydroergotamine Mesylate in Refractory Headaches," Headache 32(1):21-23.
Lahiere, R.J. et al. (Oct. 1987). "Mass-Transfer Efficiencies of Column Contactors in Supercritical Extraction Service." Ind. Eng. Chem. Res. 26(10):2086-2092.
Larson, K.A. et al. (Jun. 1986). "Evaluation of Supercritical Fluid Extraction in the Pharmaceutical Industry," Biotechnology Progress 2(2):73-82.
Lee, S-W. et al. (Apr. 1976). "Development of an Aerosol Dosage Form Containing Insulin," Journal of Pharmaceutical Sciences 65(4):567-572.
Lipton, R.B. et al. (Jul./Aug. 2001). "Migraine Diagnosis and Treatment: Results From the American Migraine Study II," Headache 41(7):638-645.
Loth, H. et al. (1986). "Properties and Dissolution of Drugs Micronized by Crystallization from Supercritical Gases," International Journal of Pharmaceutics 32:265-267.
Manivet, P. et al. (Mar. 31, 2000). "PDZ-Dependent Activation of Nitric-Oxide Synthases by the Serotonin 2B Receptor," J. Biol. Chem. 275(13):9324-9331.
Mathew, N. T. et al. (May 1996). "Coexistence of Migraine and idiopathic Intracranial Hypertension without Papilledema," Neurology 46:1226-1230.
Matson, D.W. et al. (Jun. 1987). "Production of Powders and Films by the Rapid Expansion of Supercritical Solutions," Journal of Materials Science 22(6):1919-1928.
McCarthy, B.G. et al. (Jul. 1989). "Comparative Neuropharmacology of Dihydroergotamine and Sumatriptan (GR 43175)," Headache 29(7):420-422.
McGirt, M.J. et al. (Nov. 2002). "Serum Von Willebrand Factor, Matrix Metalloproteinase-9, and Vascular Endothelial Growth Factor Levels Predict the Onset of Cerebral Vasospasm After Aneurysmal Subarachnoid Hemorrhage," Neurosurgery 51(5):1128-1135.
Meyer, J.D. et al. (Sep. 1998). "Preparation and in vitro Characterization of Gentamycin-Impregnated Biodegradable Beads Suitable for Treatment of Osteomyelitis." Journal of Pharmaceutical Sciences 87(9):1149-1154.
Mohamed, R.S. et al. (1989). "Solids Formation After the Expansion of Supercritical Mixtures" Chapter 23 in ACS Symposium Series 406, Supercritical Fluid Science and Technology, Johnston, K.P. et al. eds., American Chemical Society: Washington, DC, pp. 355-378.
Moskowitz, M.A. (Aug. 1992). "Neurogenic Versus Vascular Mechanisms of Sumatriptan and Ergot Alkaloids in Migraine," Trends Pharmacol. Sci. 13(8):307-311.
International Preliminary Report on Patentability mailed Aug. 20, 2009, for PCT Application No. PCT/US2008/001829 filed Feb. 11, 2008, 6 pages.
Advisory Action mailed Jan. 25, 2012, for U.S. Appl. No. 12/548,304, filed Aug. 26, 2009, 3 pages.
Response to Office Action filed Feb. 10, 2012, for U.S. Appl. No. 12/584,395, filed Sep. 3, 2009, 9 pages.

(56) References Cited

OTHER PUBLICATIONS

Final Office Action filed Apr. 4, 2012, for U.S. Appl. No. 12/584,395, filed Sep. 3, 2009, 10 pages.
Response to Final Office Action filed Jun. 4, 2012, for U.S. Appl. No. 12/584,395, filed Sep. 3, 2009, 13 pages.
RCE & Amendment filed Oct. 5, 2012, for U.S. Appl. No. 12/548,304, filed Aug. 26, 2009, 17 pages.
Response to Office Action filed Oct. 16, 2012, for U.S. Appl. No. 11/717,276, filed Mar. 13, 2007, 9 pages.
RCE & Amendment filed Nov. 21, 2012, U.S. Appl. No. 12/584,395, filed Sep. 3, 2009, 14 pages.
Final Office Action mailed Jan. 24, 2013, for U.S. Appl. No. 11/717,276, filed Mar. 13, 2007, 8 pages.
Non-final Office Action mailed Mar. 4, 2013, for U.S. Appl. No. 12/584,395, filed Sep. 3, 2009, 14 pages.
RCE & Amendment filed Nov. 21, 2012, for U.S. Appl. No. 12/584,395, filed Sep. 3, 2009, 14 pages.
Non-final Office Action mailed Mar. 4, 2013, for U.S. Appl. No. 12/584,395, filed Sep. 3, 2009,14 pages.
Final Office Action mailed Nov. 27, 2012, for U.S. Appl. No. 12/823,981, filed Jun. 25, 2010, 23 pages.
Anonymous. (2000). "The Headaches," Olesen, J. et al. eds., 2$^{nd}$ edition. Lippincott Williams & Wilkins, Philadelphia PA, 10 pages. (Table of Contents Only).
Anonymous. (2004). "Migraine" Part 1 in *The International Classification of Headache Disorders* 2$^{nd}$ Edition, *Cephalalgia* 24(Suppl 1) 9-160. (Table of Contents Only).
Berge, S.M. et al. (1977). "Pharmaceutical Salts" *J. Pharm. Sci.* 66(1):1-19.
Bigal, M.E. et al. (Jul. 25, 2006). "Age-Dependent Prevalence and Clinical Features of Migraine". *Neurology* 67(2):246-251.
Bradford, M. M. (1976). "A Rapid and Sensitive Method for the Quantitation of Microgram Quantities of Protein Utilizing the Principle of Protein-Dye Binding," *Analytical Biochemistry* 72:248-254.
Chapman, K.R. et al. (2006). "Inhaler choice in primary practice" *Eur. Respir. Rev.* 14(96):117-122.
Cho, I. J. et al. (2008, e-published Aug. 19, 2008). "The Identification of C/EBPβ as a Transcription Factor Necessary for the Induction of MAPK Phosphatase-1 by Toll-Like Receptor-4 Ligand," *Archives of Biochemistry and Biophysics* 479:88-96.
D'Alesandro, R. et al. (1983). "Menstrual Migraine: Intermittent Prophylaxis With a Timed-Release Pharmacological Formulation of Dihydroergotamine," *Cephalalgia* Suppl. 1:156-158.
Doods, H. et al. (2000). "Pharmacological Profile of BIBN4096Bs, the First Selective Small Molecule CGRP Antagonist," *British Journal of Pharmacology* 129(3):420-423.
Edvinsson, L. et al. (1994). "Neuropeptides in Migraine and Cluster Headache," *Cephalalgia* 14:320-327.
Ferrari, M.D. et al. (1995). "5-HT$_1$ Receptors in Migraine Pathophysiology and Treatment," *European Journal of Neurology* 2:5-21.
Frijns, C.J.M. et al. (2006). "Early Circulating Levels of Endothelial Cell Activation Markers in Aneurysmal Subarachnoid Haemoorrhage: Associations with Cerebral Ischaemic Events and Outcome," *J. Neurol. Neurosurg. Psychiatry* 77:77-83.
Frijns, C.J.M. et al. (2006). "Endothelial Cell Activation Markers and Delayed Cerebral Ischaemia in Patients with Subarachnoid Haemorrhage," *J. Neurol. Neurosurg. Psychiatry* 77:863-867.
Gallagher, P.E. et al. (Nov. 2008, e-pub. Sep. 3, 2008). "MAP Kinase/Phosphatase Pathway Mediates the Regulation of ACE2 by Angiotensin Peptides," *Am. J. Physiol. Cell Physiol.* 295:C1169-C1174.
Johansson-Haque, K. et al. (2008). "Stimulation of MAPK-Phosphatase 1 Gene Expression by Glucocorticoids Occurs Through a Tethering Mechanism Involving C/EBP," *Journal of Molecular Endocrinology* 41:239-249.
Johnson, K.W. et al. "Serotonin in Migraine: Theories, Animal Models and Emerging Therapies," vol. 51 in *Progress in Drug Research*, Jucker, E. ed., Birkhäuser Verlag: Basel, Germany, pp. 221-224.

Jeunne, C.L. et al. (1999). "Comparative Efficacy and Safety of Calcium Carbasalate Plus Metoclopramide Verus Ergotamine Tartrate Plus Caffeine in the Treatment of Acute Migraine Attacks," *Eur. Neurol.* 41:37-43.
Kelman, L. (Oct. 2004). :"The Premonitory Symptoms (Prodrome): A Tertiary Care of 893 Migrainueurs," *Headache* 44 865-872.
Massiou, H. (1987). "Dihydroergotamine Nasal Spray in Prevention and Treatement of Migraine Attacks: Two Controlled Trials Versus Placebo," *Cephalaglgia* pp. 440-441.
Mather, P.J. et al. (Sep. 1991). "The Treatment of Cluster Headaches With Repetitive Intravenous Dihydroergotamine" *Headache* 31:525-532.
Pradalier, A. et al. (2004). "The Promise Study: PROphylaxis of Migraine with SEglor® (Dihydroergotamine Mesilate) in French Primary Care" *CNS Drugs* 18(15):1149-1163.
Read, S.J. et al. (1997). "Furosemide Inhibits Regenerative Cortical Spreading Depression in Anaesthetized Cats," *Cephalalgia* 17:826-832.
Rosen, T.D. (Sep. 12, 2000). "Treatment of a Prolonged Migrainous Aura with Intravenous Furosemide," *Neurology* 55(5):732-733.
Schaerlinger, B. et al. (Sep. 2003). "Agonist Actions of Dihydroergotamine at 5-HT$_{2B}$ and 5-HT$_{2C}$ Receptors and Their Possible Relevance to Antimigraine Efficacy," *British Journal of Pharmacology* 140(2):277-284.
Tietjen, G.E. (2000). "The Relationship of Migraine and Stroke," *Neuroepidemiology* 19:13-19.
Tietjen, G.E. (2005). "The Risk of Stroke in Patients with Migraine and Implications for Migraine Management," *CNS Drugs* 19(8):683-692.
Welch, K.M.A. (1997). "Pathogenesis of Migraine," *Seminars in Neurology* 17(4):335-341.
Wyss, P.A. et al. (1991). "Pharmacokinetic Investigation of Oral and IV Dihydroergotamine in Healthy Subjects," *Eur. J. Clin. Pharmacol.* 41(6):597-602.
Yaglom, J. et al. (Jun. 2003). "Inactivation of Dual-Specificity Phosphatases is Involved in the Regulation of Extracellular Signal-Regulated Kinases by Heat Shock and Hsp72," *Molecular and Cellular Biology* 23(11):3813-3824.
Non-Final Office Action mailed on Apr. 29, 2010, for U.S. Appl. No. 12/069,667, filed Feb. 11, 2008, 8 pages.
Non-Final Office Action mailed on Jul. 21, 2010, for U.S. Appl. No. 12/548,304, filed Aug. 26, 2009, 13 pages.
Non-Final Office Action mailed on Jul. 22, 2010, for U.S. Appl. No. 12/548,292, filed Aug. 26, 2009, 13 pages.
International Search Report and Written Opinion mailed on Aug. 30, 2010, for PCT Patent Application No. PCT/US2010/040048, filed on Jun. 25, 2010, 7 pages.
Non-Final Office Action mailed on Sep. 1, 2010, for U.S. Appl. No. 10/572,012, filed Oct. 10, 2007, 14 pages.
Response to Non-Final Office Action mailed on Sep. 29, 2010, for U.S. Appl. No. 12/069,667, filed Feb. 11, 2008, 10 pages.
Non-Final Office Action mailed on Oct. 7, 2010, for U.S. Appl. No. 12/839,190, filed Jul. 19, 2010, 7 pages.
Supplemental Response to Non-Final Office Action mailed on Nov. 8, 2010, for U.S. Appl. No. 12/069,667, filed Feb. 11, 2008, 7 pages.
Response to Non-Final Office Action mailed on Jan. 20, 2011, for U.S. Appl. No. 12/548,304, filed Aug. 26, 2009, 17 pages.
Response to Non-Final Office Action mailed on Jan. 20, 2011, for U.S. Appl. No. 12/548,292, filed Aug. 26, 2009, 16 pages.
Non-Final Office Action mailed on Mar. 3, 2011, for U.S. Appl. No. 12/069,667, filed Feb. 11, 2008, 13 pages.
Response to Non-Final Office Action mailed on Mar. 7, 2011, for U.S. Appl. No. 12/839,190, filed Jul. 19, 2010, 11 pages.
Notice of Allowance mailed on Mar. 28, 2011, for U.S. Appl. No. 12/548,292, filed Aug. 26, 2009, 7 pages.
Non-Final Office Action mailed on Mar. 29, 2011, for U.S. Appl. No. 12/592,287, filed Nov. 19, 2009, 18 pages.
Non-Final Office Action mailed on Apr. 5, 2011, for U.S. Appl. No. 12/548,304, filed Aug. 26, 2009, 28 pages.
Non-Final Office Action mailed on Apr. 28, 2011, for U.S. Appl. No. 12/839,190, filed Jul. 19, 2010, 14 pages.
Response after Notice of Allowance mailed on Jun. 2, 2011, for U.S. Appl. No. 12/548,292, filed Aug. 26, 2009, 7 pages.

(56) References Cited

OTHER PUBLICATIONS

Non-Final Office Action mailed on Aug. 11, 2011, for U.S. Appl. No. 12/584,395, filed Sep. 3, 2009, 21 pages.
Response to Non-Final Office Action mailed on Aug. 29, 2011, for U.S. Appl. No. 12/592,287, filed Nov. 19, 2009, 12 pages.
Response to Non-Final Office Action mailed on Aug. 29, 2011, for U.S. Appl. No. 12/069,667, filed Feb. 11, 2008, 21 pages.
Response to Non-Final Office Action mailed on Aug. 29, 2011, for U.S. Appl. No. 12/839,190, filed Jul. 19, 2010, 20 pages.
Response to Non-Final Office Action mailed on Sep. 6, 2011, for U.S. Appl. No. 12/548,304, filed Aug. 26, 2009, 31 pages.
Written Opinion mailed on Jun. 9, 2008, for PCT Application No. PCT/US2008/001829, filed on Feb. 11, 2008, 5 pages.
Final Office Action mailed on Oct. 6, 2011, for U.S. Appl. No. 12/592,287, filed Nov. 19, 2009, 26 pages.
Final Office Action mailed on Nov. 3, 2011, for U.S. Appl. No. 12/839,190, filed Jul. 19, 2010, 10 pages.
Non-Final Office Action mailed on Nov. 3, 2011, for U.S. Appl. No. 12/069,667, filed Feb. 11, 2008, 8 pages.
Final Office Action mailed on Nov. 8, 2011, for U.S. Appl. No. 12/548,304, filed Aug. 26, 2009, 30 pages.
Response After Non-Final Office Action mailed on Dec. 12, 2011, for U.S. Appl. No. 12/069,667, filed Feb. 11, 2008, 10 pages.
Response After Final Office mailed Dec. 12, 2011, for U.S. Appl. No. 12/839,190, filed Jul. 19, 2010, 8 pages.
Notice of Allowance mailed on Jan. 3, 2012, for U.S. Appl. No. 12/839,190, filed Jul. 19, 2010, 8 pages.
Response to Final Office Action mailed Jan. 9, 2012, for U.S. Appl. No. 12/548,304, filed Aug. 26, 2009, 13 pages.
Notice of Appeal mailed Mar. 5, 2012, for U.S. Appl. No. 12/548,304, filed Aug. 26, 2009, 1 page.
Notice of Appeal mailed Apr. 5, 2012, for U.S. Appl. No. 12/592,287, filed Nov. 19, 2009, 2 pages.
RCE & Amendment filed Oct. 5, 2012, for U.S. Appl. No. 12/548,304, 14 pgs.
RCE & Amendment filed Oct. 5, 2012, for U.S. Appl. No. 12/592,287, 13 pgs.
Johnson, K.W. et al. (1998). "Serotonin in Migraine: Theories, Animal Models and Emerging Therapies," vol. 51 in Progress in Drug Research, Jucker, E. ed., Birkhäuser Verlag: Basel, Germany, pp. 221-244.
Mathew, N.T. (Jan. 1997). "Dosing and Administration of Ergotamine Tartrate and Dihydroergotamine," Headache 37(1):S26-S32.
U.S. Appl. No. 13/406,391, filed Feb. 27, 2012.
Berge, Stephen M., Pharmaceutical Salts, Journal of Pharmaceutical Sciences, Jan. 1977, 1-19, 66 (1), US.
International Search Report and the Written Opinion of the International Search Authority or the Declaration mailed Apr. 22, 2014, for PCT Application No. PCT/US2013/76420 filed Dec. 19, 2013, 10 pages.

* cited by examiner

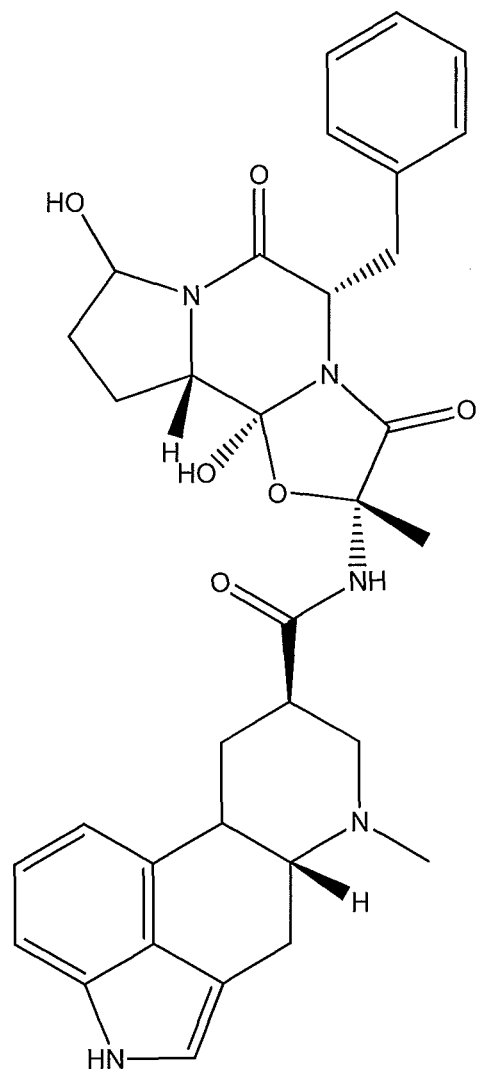

8'-HYDROXY-DIHYDROERGOTAMINE COMPOUNDS AND COMPOSITIONS

This application claims priority under 35 U.S.C. §119(e) from U.S. Provisional Application Ser. No. 61/745,104, filed Dec. 21, 2012, which is hereby incorporated by reference in its entirety.

TECHNICAL FIELD OF THE INVENTION

Provided herein are 8'-Hydroxy-Dihydroergotamine (8'-OH DHE) medicinal compounds, compositions, and dosage forms containing such compositions. Also provided herein are methods of treatment, prevention, or amelioration of migraine disorders using the compounds, compositions and dosage forms disclosed herein. Still further provided herein are methods of agonizing receptors such as, for example, the $5\text{-HT}_{1D}$ and/or the $5\text{-HT}_{1B}$ receptor, without agonizing the $5\text{-HT}_{2B}$ receptor using the compounds, compositions and dosage forms disclosed herein. In addition, provided herein are methods of antagonizing or inhibiting activity at receptors such as, for example, the adrenergic $\text{alpha}_{2A}$ and/or the $\text{alpha}_{2B}$ receptors using the compositions and dosage forms disclosed herein.

BACKGROUND OF THE INVENTION

Migraine is the most common headache causing patients to consult a physician. According to the American Migraine Study II, approximately 28 million people in the United States aged 12 and older (approximately 13 percent of the population) suffer from headaches that fit the medical definition of migraine established by the International Headache Society. This corresponds to one migraine sufferer in every four U.S. households. The percentage of patients whose headaches fit the medical definition of migraine who are being diagnosed has increased compared to a decade ago. A majority of all migraine sufferers (53 percent) characterize their pain as causing either severe impairment or forcing them to retreat to their beds sometimes for days at a time. There have been no dramatic changes in the way physicians approach the treatment of migraine in the past 10 years. (Lipton et al., Headache 41:638-645, 646-657 (2001)), A three-item Identification of Migraine (ID Migraine) clinical decision rule for the diagnosis of migraine has been developed (Stewart et al., Neurology 44(6 suppl 4):S17-23 (1994)). A migraine is a type of primary headache that some people get repeatedly over time. Migraines are different from other headaches because they occur with symptoms such as nausea, vomiting, or sensitivity to light. In most people, a throbbing pain is felt only on one side of the head. Migraines are classified as either "with aura" or "without aura." An aura is a group of neurological symptoms, usually vision disturbances that serve as warning sign. Patients who get auras typically see a flash of brightly colored or blinking lights shortly before the headache pain begins. However, most people with migraines do not have such warning signs.

Multiple humoral agents have been postulated as being the major factor in migraine. These include serotonin, histamine, prostaglandins, platelet factors, endorphins, and vasoactive neuropeptides. The etiology of migraine has been studied by many investigators. Present research no longer fully supports the vasodilator/vasoconstrictor mechanism of vascular headache, i.e., arterial dilation causes pain and constriction equals relief. Research also has now implicated a sterile inflammation, possibly occurring in the dura mater, as the causative factor for vascular head pain. An unknown trigger activates perivascular trigeminal axons, which release vasoactive neuropeptides (substance P, calcitonin gene-related peptide, etc.). These agents produce the local inflammation, i.e., vasodilation, plasma extravasation and mast cell degranulation, which cause transmission of impulses to the brain stem and higher centers which in turn register as head pain (Moskowitz, M. A., Trends Pharmacol. Sci. 13:307-311 (1992)).

Migraine therapy is either prophylactic or acute (symptomatic). Prophylactic medication may be selected for a patient having two to four or more headaches per month, if they are severe enough to interfere with daily activities. Beta blockers such as propranolol are the most commonly used. Other medications frequently used include serotonin antagonists such as methysergide, calcium channel blockers, amytryptyline, and ergotamine preparations with belladona alkaloids and phenobarbital. All of these medications have significant side effects including sedation, loss of energy and drive, dry mouth, constipation, weight gain, and gastrointestinal cramping and distress. More recently, multiple injections of the bacterial toxin onabotulinumtoxinA have been indicated for the treatment of chronic migraine. For symptomatic treatment, ergotamine with caffeine is commonly used. Other medications employed for treating migraine include isometheptene, non-steroidal anti-inflammatory drugs, dihydroergotamine and the newer triptans, such as sumatriptan, etc. When narcotics, such as butalbital with codeine are used frequently, additional hazards, including the considerable potential for rebound headaches and habituation are encountered.

The administration of serotonin agonists is well established for the treatment of migraine headache. The serotonin agonist class that is most widely prescribed is the triptan class, including sumatriptan, zolmitriptan, naratriptan, rizatriptan, eletriptan, frovatriptan and almotriptan. These compounds bind specifically to serotonin $5\text{-HT}_{1D/1B}$ receptors. To a lesser degree, ergot alkaloids such as ergotamine and dihydroergotamine (DHE) are also used to treat a variety of disease states, including, but not limited to the acute treatment of migraine.

Dihydroergotamine (DHE) was identified as an effective treatment for migraine nearly fifty years ago (Raskin, Neurology 36:995-997 (1986); Silberstein, et al., Headache 30:334-339 (1990); Saadah, Headache 32:18-20 (1992); and Winner, Headache 33:471-475 (1993)). DHE has been administered by intramuscular (IM) or intravenous (IV) injection for over 50 years (Belgrade, et al., Neurology 39:590-592 (1989) and Winner, Headache 33:471-475 (1993)). More recently, DHE has been administered using alternative delivery techniques such as intranasal (IN) administration or subcutaneous (SC) injection (Klapper, et al., Headache 32:21-23 (1992); Winner, et al., Arch. Neurol. 53:180-184 (1996); and Becker, et al., Headache 36:144-148 (1996)). In addition, an oral inhalation dosage form of DHE has been developed that is administered using a breath-actuated, pressurized metered dose inhaler (pMDI) device (U.S. Publication No. US2008/0287451 to Cook et al.).

Although effective in the treatment of migraine, DHE administration is often accompanied by side effects such as nausea, vomiting and chest pain (Winner, et al., Arch. Neurol. 53:180-184 (1996)). Other side effects observed from post-marketing experience in patients receiving DHE injection include vasospasm, paraesthesia, hypertension, dizziness, anxiety, dyspnea, headache, flushing, diarrhea, rash, increased sweating, cardiac valvulopathy, and pleural and retroperitoneal fibrosis seen after long-term use of dihydroergotamine. At least one side effect, nausea, occurs more frequently after intravenous administration than after intramuscular or intranasal administration. When given subcutaneously at a concentration of only 1.5 mM, DHE has been reported to cause nausea in nearly 16% of treated patients (Winner, et al., *Arch. Neurol.* 53: 180-184 (1996)). The currently accepted treatment algorithms for injection or IV use of DHE call for the administration of an antiemetic prior to or concurrent with administration of DHE to prevent nausea. Due to the possibility for fibrotic side effects, patients with known cardiovascular disease are not qualified to receive IV DHE treatment. Notwithstanding the potential for such undesirable side effects, DHE is still considered the "gold standard" for treatment of severe migraine, cluster headache, and chronic daily headache.

With regard to considerations of absorption, distribution, metabolism, and excretion (ADME), DHE has a very low oral bioavailability (i.e., from 1-3%) due to a high first-pass metabolism and incomplete drug passage across the gastrointestinal mucosa (Little et al., *Br J Clin Pharmacol.* 15:785-790 (1982)), whereas the bioavailability of IM DHE is 100%, and about 40% following IN administration (Silberstein et al. *Headache* 43:144-166 (2003)). Although little is known about human tissue distribution, DHE can be found distributed in high concentrations in the liver, lung and kidney after oral or IV administration in rats. DHE is quickly and extensively metabolized in the liver, and only about 6-7% of an IM administered DHE dose is extracted in the urine. The major elimination route is in the feces following biliary excretion of the parent DHE and its metabolites. (Silberstein et al. *Headache* 43:144-166 (2003)). Four DHE metabolites have been identified in human plasma following oral administration (Maurer et al., *Pharmacology* 26:463-470 (1984)), however only those metabolites that retain the essential ring structures of the ergot alkaloids (the ergoline ring and the peptide side chain) are pharmacologically active. In this regard the major metabolite appears to be the 8'-OH DHE metabolite (Chen et al. J., *Chromatography* 768:267-275 (2002)) which is an active metabolite having pharmacologic effects that are qualitatively similar to that of the parent DHE compound (Moller-Schweinitzer E., *Eur J Clin Pharmacol* 26:699-705 (1984) and Hanoun et al., *Br J Pharmacol* 139:424-434 (2003)).

SUMMARY OF THE INVENTION

The invention relates to 8'-Hydroxy-Dihydroergotamine (8'-OH DHE) medicinal compounds, compositions, and dosage forms containing such compositions. The invention further relates to methods of treatment, prevention, or amelioration of migraine disorders using the 8'-OH DHE compounds, compositions, dosage forms and administration techniques as described herein.

It is accordingly a primary object of the invention to provide medicinal 8'-OH DHE compositions that comprise an 8'-OH DHE compound. In such compositions, the 8'-OH DHE compound has been rendered suitable for use as a pharmaceutical product by: (a) conversion to a pharmaceutically acceptable salt, solvate, ester or hydrate of the parent 8'-OH DHE molecule; (b) conversion to the free base form; conversion into a pharmaceutical dosage form such as a solid particulate form (amorphous, semicrystalline or crystalline); and/or by combination with any pharmaceutical vehicle and/or excipient.

It is a related object of the invention to provide 8'-OH DHE derivatives, wherein the parent 8'-OH DHE molecule has been chemically altered such that one or more positions on the ergoline ring and/or the peptide side chain have been substituted.

In certain aspects of the invention, the specific substitution or substitutions to the parent 8'-OH DHE molecule in the resulting 8'-OH DHE derivatives can provide for a reduction in a drug-induced side effect such as fibrosis, for example when the substitution or substitutions are suitable to reduce or eliminate agonism at the 5-HT$_{2B}$ receptor. In other aspects of the invention, the specific substitution or substitutions to the parent 8'-OH DHE molecule in the resulting 8'-OH DHE derivatives can provide for enhanced antagonizing activity at migraine-related receptors including 5-HT$_{2B}$ receptors and adrenergic alpha$_{1A}$, alpha$_{1D}$, alpha$_{2C}$, alpha$_{2A}$ and alpha$_{2B}$ receptors. In still further aspects of the invention, the specific substitution or substitutions to the parent 8'-OH DHE molecule in the resulting 8'-OH DHE derivatives can provide for enhanced agonizing activity at the 5-HT$_{1D}$ and 5-HT$_{1B}$ receptors, including enhancement in selective agonizing activity at the 5-HT$_{1D}$ receptor over the 5-HT$_{1B}$ receptor. In addition, the specific substitution or substitutions to the parent 8'-OH DHE molecule in the resulting 8'-OH DHE derivatives can provide for reduction the agonism activity of dopamine receptors when compared to agonism of dopamine receptors by other ergolines, such as, for example, DHE. In one particular example, the substitution results in a reduction in agonism activity at the D$_{2L}$ and D$_4$ dopamine receptors.

It is also a primary object of the invention to provide methods of treating a migraine disease, condition and/or disorder by administering a therapeutically effective amount of an 8'-OH DHE compound (including, e.g, an 8'-OH DHE derivative), an 8'-OH DHE composition, or any pharmaceutical dosage form comprising such molecules to a subject in need of treatment. In the practice of the methods of the invention, the 8'-OH DHE compound or composition (or any formulation thereof) can be administered in the form of any suitable pharmaceutical preparation. In the practice of such treatment methods, therapeutically effective amounts of the 8'-OH DHE compounds or compositions as described herein are administered to a subject in need of treatment.

In certain aspects of the invention, administration of the 8'-OH DHE compound or composition is carried out to reduce a migraine symptom within a specified time period, for example, where a suitable migraine treatment involves the provision of partial relief from at least one migraine syndrome. In this regard, reduction of a migraine symptom can further comprise providing sustained relief for extended periods of time.

In another aspect of the invention, methods of treating, preventing, or ameliorating one or more symptoms of migraine disease, conditions or disorders while at the same time avoiding the inducement of one or more drug-induced side effects are provided. In practicing such treatment methods, therapeutically effective amounts of the 8'-OH DHE compounds or compositions as described herein are administered to a subject in need of treatment using optimized 8'-OH DHE compositions (e.g., 8'-OH DHE derivatives) and/or dosage forms containing such compositions.

The subject methods of the invention can further involve administration of therapeutically effective amounts of the 8'-OH DHE compound or composition, where the rate of administration does not result in one or more of drug-induced nausea, emesis, chest tightness and related cardiovascular effects such as blood pressure instability, venous and arterial constriction, or any other adverse effects known to be associated with treatment of migraine with commercially available DHE compounds or compositions.

In one aspect, the invention provides methods for providing an amount of the 8'-OH DHE compound to a subject at a selected rate sufficient to develop a circulating plasma concentration level of 8'-OH DHE effective for the 8'-OH DHE to act as an agonist against a serotonin receptor related to alleviating a migraine symptoms (wherein the 8'-OH DHE $C_{max}$ is attained within a time period ($T_{max}$) sufficient for providing partial relief from at least one migraine syndrome including but not limited to pain, nausea, phonophobia and photophobia, within a period of about 30, 60, 90, 120 or 180 minutes or less, or providing sustained relief for about 3, 6, 12, 18, 24 or 36 hours or more), while at the same time the 8'-OH DHE $C_{max}$ is kept low enough so as to remain insufficient for active binding of the 8'-OH DHE to an adrenergic or dopaminergic receptor to cause nausea and other unwanted drug-induced side effects. For example, the 8'-OH DHE composition can be administered at a rate such that the 8'-OH DHE $C_{max}$ is less than about 500, 1000, 1500, 2500, 5,000; 7,500; 10,000; 15,000; 20,000; 25,000; 30,000; 40,000 or 50,000 pg/mL. In one particular example, the 8'-OH DHE composition is administered at a rate such that the 8'-OH DHE $C_{max}$ is less than about 4,500; 4,000; 3,500, 3,000, 2,500, 2,000 or 1,500 pg/mL.

One particularly preferred method of carrying out the methods of the invention is to administer the 8'-OH DHE compound or composition using oral pulmonary inhalation from a DPI or pMDI inhaler device. In one particular aspect of the invention, a pharmaceutically acceptable salt of the 8'-OH DHE compound is converted into crystalline particles to provide a stable dry powder form of 8'-OH DHE that is suitable for use in a propellant suspension for administration via pulmonary aerosol inhalation. The 8'-OH DHE powder can be suspended in an HFA propellant doses thereof can be administered via oral pulmonary inhalation using a breath-actuated pMDI device such as the TEMPO® Inhaler (MAP Pharmaceuticals, Inc., Mountain View, Calif. 94043 USA).

It is a further object of the invention to provide methods for antagonizing receptors including 5-$HT_{2B}$ receptors and adrenergic $alpha_{1A}$, $alpha_{1D}$, $alpha_{2c}$, $alpha_{2A}$ and $alpha_{2B}$ receptors using the 8'-OH DHE compounds and compositions as described herein. In practicing the methods, therapeutically effective amounts of the compounds or compositions are administered.

A related object of the invention is to provide methods for agonizing the 5-$HT_{1D}$ and 5-$HT_{1B}$ receptors using the compounds and compositions described herein. In some aspects of the invention, methods of selectively agonizing the 5-$HT_{1D}$ receptor over the 5-$HT_{1B}$ receptor using the 8'-OH DHE compounds and compositions described herein are provided.

In still other aspects of the invention, methods of reducing agonism of dopamine receptors when compared to agonism of dopamine receptors by other ergolines, such as, for example, DHE using the compounds and compositions described herein is provided herein. In some examples, the reduced agonism is at the $D_{2L}$ and $D_4$ dopamine receptors. In practicing the methods, therapeutically effective amounts of the compounds or compositions are administered.

The present invention and other objects, aspects, and advantages of the present invention will become further apparent in the following Detailed Description of the Invention and the accompanying FIGURES.

BRIEF DESCRIPTION OF THE DRAWINGS

FIG. 1 depicts the chemical structure of 8'-Hydroxy-Dihydroergotamine (8'-OH DHE).

DETAILED DESCRIPTION OF THE INVENTION

Definitions

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. For example, an alkyl group can comprise from 1 to 20 carbon atoms ($C_1$-$C_{20}$ alkyl). In other examples, an alkyl group comprises from 1 to 10 carbon atoms ($C_1$-$C_{10}$ alkyl). In still other examples, an alkyl group comprises from 1 to 6 carbon atoms ($C_1$-$C_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{400}$, where $R^{400}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. For example, an aryl group comprises from 6 to 20 carbon atoms ($C_6$-$C_{20}$ aryl). In other examples, an aryl group comprises from 6 to 15 carbon atoms ($C_6$-$C_{15}$ aryl). In still other examples, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

The term "composition", and in particular the term "8'-OH DHE composition" refers to an 8'-OH DHE compound as defined herein where that molecule has been converted into a pharmaceutically acceptable form, for example, by formation of a pharmaceutically acceptable salt, solvate, ester or hydrate of an 8'-OH DHE molecule, by conversion to the free base form, or by conversion of an 8'-OH DHE compound into a pharmaceutical dosage form such as a solid particulate form (amorphous, semicrystalline or crystalline), or by combination with any pharmaceutical vehicle and/or excipient and thus rendered suitable for use as a pharmaceutical product.

"Compound", and particularly "8'-OH DHE compound" refers to the 8'-OH DHE molecules as disclosed herein and includes any specific derivative compounds (i.e., any "8'-OH DHE derivative" as defined herein below) and whose structure is disclosed herein. Compounds may be identified either by their chemical structure and/or chemical name. When the chemical structure and chemical name conflict, the chemical structure is determinative of the identity of the compound. The 8'-OH DHE compounds described herein may contain one or more chiral centers and/or double bonds and therefore, may exist as stereoisomers, such as double-bond isomers (i.e., geometric isomers), enantiomers or diastereomers. Accordingly, any chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The 8'-OH DHE compounds may also exist in several tautomeric forms including the enol form, the keto form and mixtures thereof. Accordingly, any chemical structures depicted herein encompass all possible tautomeric forms of the illustrated compounds. The 8'-OH DHE compounds described also include isotopically labeled compounds where one or more atoms have an atomic mass different from the atomic mass conventionally found in nature. Examples of isotopes that may be incorporated into the compounds described herein include, but are not limited to, $^2H$, $^3H$, $^{13}C$, $^{14}C$, $^{15}N$, $^{18}O$, $^{17}O$, $^{35}S$, etc. In general, it should be understood that all isotopes of any of the elements comprising the compounds described herein may be found in these compounds. The 8'-OH DHE compounds may exist in unsolvated or unhydrated forms as well as solvated forms, including hydrated forms and as N-oxides. In general, compounds may be hydrated, solvated or N-oxides. Certain compounds may exist in multiple crystalline, semicrystalline or amorphous forms. In general, all physical forms are equivalent for the uses contemplated herein and are intended to be within the scope of the present invention.

Use of the term "derivative" and in particular an "8'-OH DHE derivative" is used herein to refer to an 8'-OH DHE molecule which has been chemically altered such that one or more positions on the ergoline ring and/or the peptide side chain have been "substituted" as defined herein below.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$—, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. For example, a heteroaryl group can comprise from 5 to 20 ring atoms (5-20 membered heteroaryl). In other examples, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. For example, the heteroarylalkyl group can be a 6-21 membered heteroarylalkyl, e.g., the alkanyl, alkenyl or alkynyl moiety of the heteroarylalkyl is $(C_1-C_6)$ alkyl and the heteroaryl moiety is a 5-15-membered heteroaryl. In other examples, the heteroarylalkyl is a 6-13 membered heteroarylalkyl, e.g., the alkanyl, alkenyl or alkynyl moiety is $(C_1-C_3)$ alkyl and the heteroaryl moiety is a 5-10 membered heteroaryl.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-Ray diffraction, X-Ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Migraine" is used herein in the broadest sense to refer to a headache disease, disorder and/or condition that fits the medical definition of migraine as established by the International Headache Society. The term thus includes so-called common migraine (typically a migraine headache not accompanied by an aura); classic migraine (a migraine headache accompanied by an aura); chronic migraine (migraine headache occurring for a greater time interval); so-called vascular headache; severe migraine, cluster headache; chronic daily headache; any migraine syndrome (e.g., pain, nausea, phonophobia, photophobia); retinal migraine; pediatric migraine; status migranosis; transformed migraine; medication overuse headache; migraine prodrome; and any other recurring and/or chronic headache or headache symptom as generally known to those of skill in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, prevention refers to reducing symptoms of the disease, condition or disorder by taking an 8'-OH DHE compound in a preventative fashion. The application of a therapeutic for preventing or prevention of a disease of disorder is known as "prophylaxis." In some embodiments, the 8'-OH DHE compounds provided herein can provide superior prophylaxis because of lower long term side effects over long time periods.

"Salt" refers to a salt of a compound, which possesses the desired pharmacological activity of the parent 8'-OH DHE compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. Preferably, the selected salt is pharmaceutically acceptable.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205-208 in *Polymorphism in Pharmaceutical Solids*, (Brittain, H. ed.), Marcel Dekker, Inc. New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-Ray diffraction, X-Ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymor-* phism in *Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =$O$, —$OR^b$, —$SR^b$, —$S^-$, =$S$, —$NR^cR^c$, =$NR^b$, =$N$—$OR^b$, trihalomethyl, —$CF_3$, —$CN$, —$OCN$, —$SCN$, —$NO$, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —$CN$, —$OCN$, —$SCN$, —$NO$, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —$CN$, —$NO$, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above. In some aspects of the invention, substituents are limited to the groups above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers to ameliorating the disease, disorder or condition (i.e., arresting or reducing the development of the disease, disorder or condition or at least one of the clinical symptoms thereof). Treatment may also be considered to include preemptive or prophylactic administration to ameliorate, arrest or prevent the development of the disease, disorder or condition, or at least one of the clinical symptoms thereof. Treatment can also refer to the lessening of the severity and/or the duration of one or more symptoms of a disease, disorder or condition. In some cases treating or treatment refers to ameliorating at least one physical parameter, which may not be discernible by the patient. In yet other examples, treating or treatment refers to inhibiting the disease, condition or disorder, either physically, (e.g., stabilization of a discernible symptom), physiologically, (e.g., stabilization of a physical parameter) or both. In yet other embodiments, treating or treatment refers to delaying the onset of the disease, condition or disorder.

"Therapeutically effective amount" means the amount of the 8'-OH DHE compound that, when administered to a patient for treating a disease, is sufficient to effect such treatment for the disease. The "therapeutically effective amount" will vary depending on the compound, the migraine disease and its severity and the age, weight, adsorption, distribution, metabolism and excretion etc., of the patient to be treated.

"Vehicle" refers to a diluent, excipient or carrier with which an 8'-OH DHE compound is administered to a subject or patient. It is preferred that the vehicle is pharmaceutically acceptable.

MODES OF CARRYING OUT THE INVENTION

Although Dihydroergotamine (DHE) is a well-established therapeutic agent for the treatment of migraine, there has been continued development of other selective agents for the treatment of migraine which have high 5-$HT_{1D}$:5-$HT_{1B}$ binding ratios such as, for example, the alkyltryptamine derivatives (125-fold selectivity, Slassi, *Bioorg. Med. Chem. Lett.* 10:1707-1709 (2000)), the indole series (300-fold selectivity, Castro, *J. Med. Chem.* 41:2667 (1998)) and from the non-indole series (>6000 fold selectivity, Ennis, *J. Med. Chem.* 41:2180 (1998)). However, strong agonism of 5-$HT_{1B}$ by non-ergoline migraine therapeutics such as, for example, sumatriptan, frequently leads to adverse cardiovascular effects due to excessive vasoconstriction (Phebus, *Cephalalgia* 17:245 (1997)). In this regard, an effective migraine agent should be selective for the 5-$HT_{1D}$ receptor over the 5-$HT_{1B}$ receptor, having at most moderate agonism of the 5-$HT_{1B}$ receptor in order to minimize non-cranial vasoconstriction. Antagonism of adrenergic receptors, such as, for example, $alpha_{1A}$, $alpha_{1D}$, $alpha_{2A}$, $alpha_{2B}$ and $alpha_{2C}$ by migraine therapeutics can reduce excessive vasoconstriction caused by strong 5-$HT_{1B}$ agonism.

On the other hand, agonism of dopamine receptors is highly unfavorable for anti-migraine compounds since nausea is a classic dopaminergic (activation of dopamine receptors) symptom and is already present in migraine. Yet another problem with many existing and experimental migraine therapeutics (and especially certain ergoline derivatives) is undesirable agonism of 5-$HT_{2B}$ receptors which is associated with cardiac and non-cardiac fibrosis, including cardiovascular valvulopathy (Rothman, *Circulation* 102:2836 (2000)). Conversely, antagonism of 5-$HT_{2B}$ receptors may offer therapeutic advantages in the treatment and/or prevention of migraine (Schaerlinger, *Br. J. Pharmacol.* 140(2):277-84, (2003)).

There has accordingly been a continuing need for new ergoline molecules as an alternative to DHE and triptans such as sumatriptan that can be used to safely treat and/or prevent migraine disease, conditions and/or disorders, and the inventors herein have identified and characterized a novel and effective family of just such compounds. In particular, in the conduct of clinical studies with DHE pharmaceuticals, it has been shown that DHE produces sustained relief of migraine pain, measured up to 48 hours, in association with a low recurrence rate. This beneficial effect has been noted despite the fact that the serum half-life of DHE is only about 10-13 hours. Accordingly, a generally accepted theory explaining the extended duration of action has been developed which believes that the extended action is due to an active DHE metabolite that has a much longer half-life than the parent DHE molecule. However, after conducting clinical studies following IV DHE and orally inhaled DHE administration, it has now been found that only the 8'-Hydroxy-Dihydroergotamine (8'-OH DHE) and dihydrolysergic acid amide (DHLSA) metabolites were present in plasma at concentrations above the lower limit for quantitation. In particular, following IV and oral inhalation administration of a 1 mg nominal dose of DHE, total DHE metabolites represented less that 5% of plasma DHE $AUC_{0-48}$. As such, the 8'-OH DHE metabolite would not be expected to provide for such pharmacological activity. These new findings are not too dissimilar with previous reports that total DHE metabolites only represented about 20-30% of plasma AUC following nasal administration of DHE (Humbert et al., *Clin Pharmacol & Therapeutics* 60(3):265-275 (1996)). It is therefore possible that metabolism in the gut contributed to the biotransformation of DHE and thus the presence of such high amounts of DHE metabolites as observed in previous studies (the 8'-OH DHE metabolite was reported at a concentration of 5 to 7 times greater than that of the parent DHE, Silberstein et al., *Headache* 43:144-166 (2003)).

The inventors have conducted a series of screening studies, discussed in detail herein, whereby the receptor binding activity of 8'-OH DHE at a series of serotonin and adrenergic receptors has been compared against that of DHE and sumatriptan. As a result of these studies, 8'-OH DHE compounds have been identified as particularly useful agents for use in the treatment of migraine disease, conditions and/or disorders. This utility finding has been made despite the apparent manufacturing difficulties inherent in using a biotransformed metabolite as an active pharmaceutical ingredient instead of, e.g., the parent DHE molecule or other existing alternatives. The 8'-OH DHE compounds of the present invention agonize $5\text{-HT}_{1D}$ and $5\text{-HT}_{1A}$ receptors, and have a similar selectivity for the $5\text{-HT}_{1D}$ receptor over the $5\text{-HT}_{1B}$ receptor to that of the parent DHE. The half-life of the 8'-OH DHE compounds of the present invention is further thought to be beneficial in the context of preventative treatment of migraine disease, conditions or disorders. The chemical structure of 8'-OH DHE is depicted in FIG. 1.

It is accordingly a primary object of the invention to provide medicinal 8'-Hydroxy-Dihydroergotamine (8'-OH DHE) compositions that comprise an 8'-OH DHE compound. In such compositions, the 8'-OH DHE compound has been converted into a pharmaceutically acceptable salt, solvate, ester or hydrate of the parent 8'-OH DHE molecule, or by conversion of an 8'-OH DHE compound into a pharmaceutical dosage form such as a solid particulate form (amorphous or crystalline) and/or combined with any pharmaceutical vehicle and/or excipient and thus rendered suitable for use as a pharmaceutical product.

It is a related object of the invention to provide 8'-OH DHE derivatives, wherein the parent 8'-OH DHE molecule has been chemically altered such that one or more positions on the ergoline ring and/or the peptide side chain have been substituted (e.g., where one or more hydrogen atoms of a specified group or radical on the parent 8'-OH DHE molecule are each, independently of one another, replaced with the same or different substituent including but not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S; or where one or more positions on the ergoline ring and/or the peptide side chain have been substituted such that one or more unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2NR^b$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined).

In certain aspects of the invention, the specific substitution or substitutions to the parent 8'-OH DHE molecule in the resulting 8'-OH DHE derivatives can provide for a reduction in a drug-induced side effect such as fibrosis, for example when the substitution or substitutions are suitable to reduce or eliminate agonism at the $5\text{-HT}_{2B}$ receptor. In other aspects of the invention, the specific substitution or substitutions to the parent 8'-OH DHE molecule in the resulting 8'-OH DHE derivatives can provide for enhanced antagonizing activity at migraine-related receptors including $5\text{-HT}_{2B}$ receptors and adrenergic $alpha_{1A}$, $alpha_{1D}$, $alpha_{2c}$, $alpha_{2A}$ and $alpha_{2B}$ receptors. In still further aspects of the invention, the specific substitution or substitutions to the parent 8'-OH DHE molecule in the resulting 8'-OH DHE derivatives can provide for enhanced agonist activity at the $5\text{-HT}_{1D}$ and $5\text{-HT}_{1B}$ receptors, including enhancement in selective agonizing activity at the $5\text{-HT}_{1D}$ receptor over the $5\text{-HT}_{1B}$ receptor. In addition, the specific substitution or substitutions to the parent 8'-OH DHE molecule in the resulting 8'-OH DHE derivatives can provide for reduction the agonism activity of dopamine receptors when compared to agonism of dopamine receptors by other ergolines, such as, for example, DHE. In one particular example, the substitution results in a reduction in agonism activity at the $D_{2L}$ and $D_4$ dopamine receptors.

The substitution or substitutions carried out on the parent 8'-OH DHE molecule to result in an 8'-OH DHE derivative can be carried out by the ordinarily skilled medicinal chemist, using standard chemistries and routine techniques and without undue effort or experimentation. In this regard, any specific substitution or substitutions to a parent 8'-OH DHE molecule that results in an 8'-OH DHE derivative in accordance with the present invention can be readily assessed for desired pharmacological activity by standard receptor screening methodologies readily available to, and routinely carried out by the ordinarily skilled person. In particular, candidate 8'-OH DHE derivatives that have been produced herein can be assessed using the specific receptor screening methods, techniques and assays as described in the working examples provided herein below. The candidate 8'-OH DHE derivatives can be compared using these methods, techniques and assays to, for example, DHE, sumatriptan, other 8'-OH DHE compounds or any other drug or molecule known to have anti-migraine effect.

It is also a primary object of the invention to provide methods of treating a migraine disease, condition and/or disorder by administering a therapeutically effective amount of an 8'-OH DHE compound (including, e.g, an 8'-OH DHE derivative), an 8'-OH DHE composition, or any pharmaceutical dosage form comprising such molecules to a subject in need of treatment. In the practice of the methods of the invention, the 8'-OH DHE compound or composition (or any formulation thereof) can be administered in the form of any suitable pharmaceutical preparation such as a solution, suspension, tablet, dispersible tablet, pill, capsule, powder, sustained release compositions or elixirs, in sterile solutions or suspensions for parenteral administration, as well as topical dosage forms, transdermal dosage forms, nasal and/or pulmonary dosage forms including forms suitable for oral inhalation via nebulizers, pressurized metered dose inhalers and dry powder inhalers. In the practice of such treatment methods, therapeutically effective amounts of the 8'-OH DHE compounds or compositions as described herein are administered to a subject in need of treatment.

In certain aspects of the invention, administration of the 8'-OH DHE compound or composition is carried out to reduce a migraine symptom within a specified time period, for example, where a suitable migraine treatment involves the provision of partial relief from at least one migraine syndrome which includes but is not limited to pain, nausea, phonophobia and photophobia, within a period of about 30, 60, 90, 120 or 180 minutes or less. In this regard, reduction of a migraine symptom further may comprise providing sustained relief for about 3, 6, 12, 18, 24 or 36 hours or longer.

In another aspect of the invention, methods of treating, preventing, or ameliorating one or more symptoms of migraine disease, conditions or disorders while at the same time avoiding the inducement of one or more drug-induced side effects are provided. In practicing such treatment methods, therapeutically effective amounts of the 8'-OH DHE compounds or compositions as described herein are administered to a subject in need of treatment using optimized 8'-OH DHE compositions (e.g., 8'-OH DHE derivatives) and/or dosage forms containing such compositions.

The subject methods of the invention can further involve administration of therapeutically effective amounts of the 8'-OH DHE compound or composition, where the rate of administration does not result in one or more of drug-induced nausea, emesis, chest tightness and related cardiovascular effects such as blood pressure instability and arterial constriction, or any other adverse effects known to be associated with treatment of migraine with commercially available DHE compounds or compositions.

In one aspect, the invention provides methods for providing an amount of the 8'-OH DHE compound to a subject at a selected rate sufficient to develop a circulating plasma concentration level of 8'-OH DHE effective for the 8'-OH DHE to act as an agonist against a serotonin receptor related to alleviating a migraine symptoms (wherein the 8'-OH DHE $C_{max}$ is attained within a time period ($T_{max}$) sufficient for providing partial relief from at least one migraine syndrome including but not limited to pain, nausea, phonophobia and photophobia, within a period of about 30, 60, 90, 120 or 180 minutes or less, or providing sustained relief for about 3, 6, 12, 18, 24 or 36 hours or more), while at the same time the 8'-OH DHE $C_{max}$ is kept low enough so as to remain insufficient for active binding of the 8'-OH DHE to an adrenergic or dopaminergic receptor to cause nausea and other unwanted drug-induced side effects. In this regard, 8'-OH DHE binding to an adrenergic or dopaminergic receptor will be insufficient to cause nausea and other drug-induced side effects when the 8'-OH DHE displays reduced (less than about 50%) or an absence of (about 20% or less) binding at dopaminergic receptors such as the $D_{2L}$ and $D_4$ receptors, and the 8'-OH DHE displays reduced (less than about 60%) or an absence of (about 20% or less) binding at adrenergic alpha$_{1A}$, alpha$_{1D}$, alpha$_{2c}$, alpha$_{2A}$ and alpha$_{2B}$ receptors. For example, the 8'-OH DHE composition can be administered at a rate such that the 8'-OH DHE $C_{max}$ is less than about 500, 1000, 1500, 2500, 5,000; 7,500; 10,000; 15,000; 20,000; 25,000; 30,000; 40,000 or 50,000 pg/mL. In one particular example, the 8'-OH DHE composition is administered at a rate such that the 8'-OH DHE $C_{max}$ is less than about 4,500; 4,000; 3,500, 3,000, 2,500, 2,000 or 1,500 pg/mL.

One particularly preferred method of carrying out the methods of the invention is to administer the 8'-OH DHE compound or composition using oral pulmonary inhalation from a DPI or pMDI inhaler device. In one particular aspect of the invention, a pharmaceutically acceptable salt of the 8'-OH DHE compound is converted into crystalline particles using the supercritical fluid processes described in International Publication No. WO2005/025506A2 to provide a stable dry powder form of 8'-OH DHE that is suitable for use in a propellant suspension for administration via pulmonary aerosol inhalation. The 8'-OH DHE powder can be suspended in an HFA propellant such as HFA 134a (1,1,1,2-tetrafluoroethane) and HFA 227e (1,1,1,2,3,3,3-heptafluoropropane) and provided either alone or as a ratio of HFA propellants to match the density of the crystal 8'-OH DHE particles (a ratio selected to ensure that the final suspension avoids detrimental sedimentation or cream which can precipitate irreversible agglomeration, and instead promotes a loosely flocculated system), which is easily dispersed when shaken. The resulting 8'-OH DHE aerosol suspension can be contained in a suitable aerosol canister containing, preferably, a primeless valve that provides discrete 1 mg nominal doses of the 8'-OH DHE compound on each actuation (about 0.45-0.65 mg actual doses) from the canister, and the doses can be administered via oral pulmonary inhalation using a breath-actuated pMDI device such as the TEMPO® Inhaler (MAP Pharmaceuticals, Inc., Mountain View, Calif. 94043 USA).

It is a further object of the invention to provide methods for antagonizing receptors including 5-HT$_{2B}$ receptors and adrenergic alpha$_{1A}$, alpha$_{1D}$, alpha$_{2c}$, alpha$_{2A}$ and alpha$_{2B}$ receptors using the 8'-OH DHE compounds and compositions as described herein. In practicing the methods, therapeutically effective amounts of the compounds or compositions are administered.

A related object of the invention is to provide methods for agonizing the 5-HT$_{1D}$ and 5-HT$_{1B}$ receptors using the compounds and compositions described herein. In some aspects of the invention, methods of selectively agonizing the 5-HT$_{1D}$ receptor over the 5-HT$_{1B}$ receptor using the 8'-OH DHE compounds and compositions described herein are provided.

In still other aspects of the invention, methods of reducing agonism of dopamine receptors when compared to agonism of dopamine receptors by other ergolines, such as, for example, DHE using the compounds and compositions described herein is provided herein. In some embodiments, the reduced agonist activity is at the D$_{2L}$ and D$_4$ dopamine receptors. In practicing the methods, therapeutically effective amounts of the compounds or compositions are administered.

Compositions and Methods of Administration.

The 8'-OH DHE compositions provided herein contain therapeutically effective amounts of one or more of the compounds provided herein that are useful in the prevention, treatment, or amelioration of one or more of the symptoms of migraine disease or disorders as described herein and a vehicle. Vehicles suitable for administration of the compounds provided herein include any such carriers known to those skilled in the art to be suitable for the particular mode of administration.

In addition, the 8'-OH DHE compounds may be formulated as the sole active ingredient in the composition or may be combined with other active ingredients. The 8'-OH DHE compounds are, in some examples, formulated into suitable preparations such as solutions, suspensions, tablets, dispersible tablets, pills, capsules, powders, sustained release compositions or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel Introduction to Pharmaceutical Dosage Forms, Seventh Edition (1999).

In the compositions of the present invention, effective concentrations of one or more 8'-OH DHE compounds or derivatives thereof is (are) mixed with a suitable vehicle. The compounds may be provided in the form of a corresponding salts, esters, enol ethers or esters, acetals, ketals, orthoesters, hemiacetals, hemiketals, acids, bases, solvates, ion-pairs, hydrates or prodrugs prior to composition, as described above. The concentrations of the compounds in the compositions are effective for delivery of an amount, upon administration that treats, leads to prevention, or amelioration of one or more of the symptoms of the migraine disease or disorder as described herein. In some examples, the compositions are formulated for single dosage administration. To formulate a composition, the weight fraction of an 8'-OH DHE compound is dissolved, suspended, dispersed or otherwise mixed in a selected vehicle at an effective concentration such that the treated condition is relieved, prevented, or one or more symptoms are ameliorated.

The active 8'-OH DHE compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some aspects of the invention, a therapeutically effective dosage should form produce a serum concentration of the 8'-OH DHE active pharmaceutical ingredient of from about 0.001 ng/ml to about 50-200 µg/ml. The compositions, in other aspects, should provide a dosage of from about 0.0001 mg to about 70 mg of the 8'-OH DHE compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The therapeutically effective amount of the 8'-OH DHE active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the 8'-OH DHE compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the 8'-OH DHE compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the 8'-OH DHE compound in the selected vehicle. The effective concentration is sufficient for ameliorating the symptoms of the disease, disorder or condition treated and may be empirically determined.

The 8'-OH DHE compositions of the invention are provided for administration to humans and animals in indication appropriate dosage forms, such as dry powder inhalers, pressurized metered dose inhalers, nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The compounds and derivatives thereof are, in some examples, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the 8'-OH DHE compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal composition. If desired, the 8'-OH DHE composition to be administered can also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing the 8'-OH DHE active ingredient present in the range of from about 0.005% to 100% weight percent (wt %) (with the balance made up from vehicle or carrier) can be easily prepared. Methods for preparation of these compositions are known to those skilled in the art. The contemplated compositions may contain from 0.001-100 wt % of the 8'-OH DHE active ingredient, from 0.1-95 wt %, or from 0.4-10 wt %.

In certain aspects of the invention, the 8'-OH DHE compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous 8'-OH DHE compositions and dosage forms, since water can facilitate the degradation of some compounds. For example, the addition of water (e.g., 5%) is widely accepted as a means of simulating long-term storage in order to determine characteristics such as shelf-life or the stability of compositions over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a composition can be of great significance since moisture and/or humidity are commonly encountered during manufacture, handling, packaging, storage, shipment, and use of compositions.

Anhydrous compositions and dosage forms provided herein can be prepared using anhydrous or low moisture-containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms suitable for use herein are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain aspects of the invention, the 8'-OH DHE compositions are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include croscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The 8'-OH DHE compounds of the invention, or derivative thereof, can be provided in an oral composition that protects it from the acidic environment of the stomach. For example, the oral composition can be formulated in an enteric coating that maintains its integrity in the stomach and releases the active compound in the intestine. The oral composition may also be formulated in combination with an antacid or other such ingredient.

When the dosage unit form is a capsule, it can contain, in addition to material of the above types, a liquid carrier such as a fatty oil. In addition, dosage unit forms can contain various other materials which modify the physical form of the dosage unit, for example, coatings of sugar and other enteric agents. The 8'-OH DHE compounds can also be administered as a component of an elixir, suspension, syrup, wafer, sprinkle, chewing gum or the like. A syrup may contain, in addition to the compounds of the invention, sucrose as a sweetening agent and certain preservatives, dyes and colorings and flavors.

The 8'-OH DHE compounds can also be mixed with other active materials which do not impair the desired pharmacological action, or with materials that supplement the desired action, such as antacids, $H_2$ blockers, and diuretics.

In the practice of the invention, the oral tablet and capsule compositions may be coated as known by those of skill in the art in order to modify or sustain dissolution of the 8'-OH DHE active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either typically two-phase oil-in-water or water-in-oil systems.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension in, for example, propylene carbonate, vegetable oils or triglycerides, is in some examples encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral compositions may be prepared by dissolving or dispersing the 8'-OH DHE compound (or salt thereof) in vegetable oils, glycols, triglycerides, propylene glycol esters (e.g., propylene carbonate) and other such carriers, and encapsulating these solutions or suspensions in hard or soft gelatin capsule shells. Other useful compositions include those set forth in U.S. Pat. Nos. RE28,819 and 4,358,603. Briefly, such compositions include, but are not limited to, those containing an 8'-OH DHE compound as described herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other suitable compositions include, but are not limited to, aqueous alcoholic solutions including an acetal. Alcohols that are used in these compositions are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some cases characterized by injection either subcutaneously, intramuscularly or intravenously is also contemplated herein. Injectable compositions can be prepared in conventional forms, either as liquid solutions or suspensions, solid forms suitable for solution or suspension in liquid prior to injection, or as emulsions. The injectables, solutions and emulsions also can contain one or more excipients. Suitable excipients are, for example, water, saline, dextrose, glycerol or ethanol. In addition, if desired, the compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release 8'-OH DHE system, such that a constant level of dosage is maintained (see, e.g., U.S. Pat. No. 3,710,795) is also contemplated herein. Briefly, a compound as provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of the 8'-OH DHE compound contained in such parenteral compositions is highly dependent on the specific nature thereof, as well as the activity of the specific compound and the needs of the subject.

Parenteral administration of the compositions of the invention includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of the 8'-OH DHE compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an 8'-OH DHE compound is an effective mode of administration. Another example is a sterile aqueous or oily solution or suspension containing the 8'-OH DHE compound injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The 8'-OH DHE compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

The 8'-OH DHE compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms and delivery devices can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release compositions known to those of ordinary skill in the art, including those described herein, can be readily selected for use with the 8'-OH DHE compounds provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release compositions include extended activity of the drug, reduced dosage frequency, and increased patient compliance. In addition, controlled-release compositions can be used to affect the time of onset of action or other characteristics, such as blood levels of the drug, and can thus affect the occurrence of side (e.g., adverse) effects.

Most controlled-release compositions are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain aspects of the invention, the 8'-OH DHE compound may be administered using intravenous infusion, an implantable osmotic pump, a transdermal patch, liposomes, or other modes of administration. In some cases, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In other examples, polymeric materials can be used. In still further examples, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The 8'-OH DHE compounds can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The 8'-OH DHE compound then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving an 8'-OH DHE compound as provided herein in a suitable solvent. The solvent can contain an excipient which improves the stability or other pharmacological component of the powder or reconstituted solution, prepared from the powder. Excipients that can be used include, but are not limited to, an antioxidant, a buffer and a bulking agent. In some examples, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired composition. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a composition for use in parenteral administration. For reconstitution, the lyophilized powder is added to sterile water or other suitable carrier. The precise amount depends upon the selected compound. Such amount can be empirically determined.

Topical mixtures containing the 8'-OH DHE compound are prepared as described herein for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other compositions suitable for topical administration.

In one aspect of the invention, the 8'-OH DHE compound or composition is delivered using inhalation therapy. Many preclinical and clinical studies with inhaled compounds have demonstrated that efficacy can be achieved both within the lungs and systemically. Moreover, there are many advantages associated with pulmonary delivery including rapid onset, the convenience of patient self-administration, the potential for reduced drug side-effects, ease of delivery by inhalation, the elimination of needles, and the like.

Oral inhalation compositions of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the 8'-OH DHE compounds or composition is the preferred physical form of the drug to confer longer product stability. Inhalation aerosols from dry powder inhalers (DPIs), nebulizers, vaporizers and pressurized metered dose inhalers (pMDIs) can generally include excipients or solvents to increase stability or deliverability of these drugs in an aerosol form. Additionally, the particle size of the drug aerosols can be controlled to provide the uptake characteristics consistent with the methods of the invention. Typically, particle sizes are controlled to desirable size distributions known by those skilled in the art. A controlled particle size for the can be selected to ensure that a significant fraction of the 8'-OH DHE is deposited in the lung. In some aspects of the invention, the 8'-OH DHE particles have a mass median aerodynamic diameter of about 0.1 to about 10 microns, in other embodiments, about 1 to about 5 microns and still other embodiments, about 1.2 to about 3 microns. For example, when using DPI's, 8'-OH DHE particles can be generated from a suitable bulk drug source by attrition processes such as grinding, micronizing, milling, or by multiphase precipitation processes such as spray drying, solution precipitation, supercritical extraction/precipitation or lyophilization to yield powders having an acceptable particle size for delivery to the lungs. As dry powder compositions are prone to aggregation and low flowability which can result in diminished efficiency, scrupulous attention is required during milling, blending, powder flow, filling and even administration to ensure that the dry powder compositions are reliably delivered and have the proper particle size distribution for delivery to the lungs.

Nebulizers generate an aerosol from a liquid, some by breakup of a liquid jet and some by ultrasonic vibration of the liquid with or without a nozzle. Liquid compositions of the 8'-OH DHE compounds of the invention are prepared and stored under aseptic or sterile conditions since they can harbor microorganisms. The use of preservatives and unit dose packaging is also contemplated. Additionally solvents, detergents and other agents can be used to stabilize the 8'-OH DHE compounds in the final drug composition.

Pressurized metered dose inhalers, or pMDIs, are an additional class of aerosol dispensing devices. The pMDI devices can house the 8'-OH DHE compound in a canister under pressure with a propellant mixture, usually chlorofluorocarbons (CFCs), or hydrofluoroalkanes (HFAs). Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds of the invention. A ratio is also selected to ensure that the final suspension avoids detrimental sedimentation or cream (which can precipitate irreversible agglomeration) and instead promote a loosely flocculated system, which is easily dispersed when shaken. Loosely flocculated systems are well regarded to provide optimal stability for pMDI canisters. As a result of the optimal flocculation properties provided by such compositions, they can be formulated to contain no ethanol and no surfactants/stabilizing agents. In the case of a solution composition, the propellant or an additional solvent can be used to dissolve the 8'-OH DHE compound. Upon being dispensed, a jet of the mixture is ejected through a valve and nozzle and the propellant "flashes off" leaving an aerosol of the 8'-OH DHE compound.

Since the parent molecule (DHE) is known to be difficult to stabilize in compositions suitable for pulmonary delivery, it may be preferable to formulate the 8'-OH DHE compound as a powder or suspension that can be stabilized without excipients or with excipients that are not toxic to the lungs. It may also be preferable to provide compositions for delivery in the form of aqueous nasal sprays or by injection, in which case chelating or complexing agents, such as dextran or cyclodextrins, can be used to stabilize the 8'-OH DHE in solution. In addition, in order to preserve the 8'-OH DHE solution from degradation, the final compositions may be sealed in a dark-glass vial that can then be opened and transferred to an injector or spray applicator immediately prior to use. Only recently stable compositions for pulmonary delivery of DHE have been described in U.S. application Ser. No. 10/572,012 and WO2005/025506A2.

International Publication No. WO2005/025506A2 describes suitable, stable compositions of DHE that can be administered as dry powders and propellant suspensions via pulmonary aerosol inhalation or nasal spray inhalation. The powders are generated using supercritical fluid processes which offer significant advantages in the production of drug particles for inhalation delivery and produce respirable particles of the desired size in a single step. This same process can be used in the practice of the instant invention in order to produce dry powders and propellant suspensions of the 8'-OH DHE compounds.

In one aspect of the invention, the 8'-OH DHE compounds can be administered via oral pulmonary inhalation using a breath-actuated pMDI device such as the TEMPO® Inhaler (MAP Pharmaceuticals, Inc., Mountain View, Calif. 94043 USA). The TEMPO pMDI device addresses limitations of standard pMDI inhalers that include inconsistent dosing and drug delivery inefficiency. The TEMPO inhalers can provide breath-actuation, enhancing patient compliance, and efficient, reliable dose-to-dose consistency that is independent of the inhalation flow rate. The TEMPO devices achieve these advantages by combining proprietary features such as a breath-synchronized trigger and a flow control chamber in a small, easy to use hand-held inhaler device. The advanced aerodynamic control elements of TEMPO inhalers are driven only by the patient's breath, avoiding expensive, power-consuming electronics, resulting in an affordable, reliable and disposable device platform.

The 8'-OH DHE compounds may alternatively be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active 8'-OH DHE compound alone or in combination with other excipients can also be administered.

For nasal administration, the preparation can contain an esterified phosphonate compound dissolved or suspended in a liquid carrier, in particular, an aqueous carrier, for aerosol application. The carrier can further contain solubilizing or suspending agents such as propylene glycol, surfactants, absorption enhancers such as lecithin or cyclodextrin, or preservatives.

8'-OH DHE solutions, particularly those intended for ophthalmic use, can be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, 8'-OH DHE dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances generally utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one example of the invention, is about 2 to 3 gm. Tablets and capsules for rectal administration are manufactured using the same substance and by the same methods as for compositions for oral administration.

In some embodiments, liposomal suspensions, including tissue-targeted liposomes, such as tumor-targeted liposomes, may also be suitable as carriers. These may be prepared according to methods known to those skilled in the art. For example, liposome compositions may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The 8'-OH DHE compounds or compositions can be packaged as articles of manufacture containing packaging material, the 8'-OH DHE compound or composition that is effective for treatment, prevention or amelioration of one or more symptoms of migraine disease or disorders within the packaging material, and a label that indicates that the 8'-OH DHE compound or composition is used for the treatment, prevention or amelioration of one or more symptoms of migraine disease or disorder.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected composition and intended mode of administration and treatment. A wide array of compositions of the compounds and compositions provided herein are contemplated as are a variety of treatments for the migraine conditions described herein.

Dosages.

In human therapeutics, the physician will determine the dosage regimen that is most appropriate according to a preventive or curative treatment and according to the age, weight, stage of the disease and other factors specific to the subject to be treated. The 8'-OH DHE compositions described above and in other embodiments, should provide a dosage of from about 0.0001 mg to about 70 mg of the active 8'-OH DHE compound per kilogram of body weight per day. Dosage unit forms are prepared to provide from about 0.01 mg, 0.1 mg or 1 mg to about 500 mg, 1000 mg or 5000 mg, and in some examples from about 10 mg to about 500 mg of the 8'-OH DHE compound or a combination of the 8'-OH DHE compound with other essential ingredients per dosage unit form. The amount of the 8'-OH DHE compound in the compositions provided herein, which will be effective in the prevention or treatment of the migraine disease, disorder or condition, or one or more symptoms thereof, will vary with the nature and severity of the disease, disorder or condition, and the route by which the 8'-OH DHE compound is administered. The frequency and dosage will also vary according to factors specific for each subject depending on the specific therapy (e.g., therapeutic or prophylactic agents) administered, the severity of the migraine disorder, disease, or condition, the route of administration, as well as age, body, weight, response, and the past medical history of the subject.

Exemplary doses of a composition include milligram or microgram amounts of the 8'-OH DHE compound per kilogram of subject (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the 8'-OH DHE compound outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such migraine disease, conditions or disorders, but insufficient to cause, or sufficient to reduce, adverse effects associated with the compositions provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain aspects of the invention, administration of the same 8'-OH DHE composition provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions.

Methods of treating, preventing, or ameliorating one or more symptoms of migraine disease, conditions or disorders are provided herein. In practicing such treatment methods, therapeutically effective amounts of the 8'-OH DHE compounds or compositions as described herein are administered to a subject in need of treatment.

In order to reduce a migraine symptom within a specified time period, a suitable treatment may involve the provision of partial relief from at least one migraine syndrome which includes but is not limited to pain, nausea, phonophobia and photophobia, within a period of about 30, 60, 90, 120 or 180 minutes or less. Reduction of a migraine symptom further may comprise providing sustained relief for about 3, 6, 12, 18, 24 or 36 hours or longer.

Relief from any of the migraine symptoms can be measured by a drop from an IHS score of greater than "0" (that is, a score of >1 for pain) at the time of administration of the 8'-OH DHE composition, to a score of ≤1 at about 30, 60, 90, 120 or 180 minutes or less following administration of the composition. However, freedom from pain (or other severe migraine symptoms) requires a reduction in grading of that symptom from an initial >0 result (that is, a score of >1 for pain) to a core of 0 at the time point in question.

More particularly, the clinical efficacy of a migraine treatment regimen can be evaluated based on primary and secondary endpoints. A primary efficacy endpoint may be a pain-free response rate at about 2 hours post-administration of the 8'-OH DHE composition. Secondary efficacy endpoints typically examine 3 areas of interest: pain-free response at time points earlier than 2 hours post-administration; non-progression of headache; and impact on normal activities.

All four migraine symptoms—pain, nausea, phonophobia and photophobia—are scored at each time point on a four point scale developed by the International Headache Society (IHS; International Headache Society Committee on Clinical Trials in Migraine. Guidelines for controlled clinical trials of drugs in migraine, 1st ed. *Cephalalgia* 11:1-12 (1991)), where scoring is:

0=none
1=mild symptom, not interfering with normal daily activities
2=moderate symptom, causing some restriction to normal activities
3=severe, leading to inability to perform normal daily activities Headache pain intensity is measured on the 4-point severity scale (0=no pain, 1=mild pain, 2=moderate pain, and 3=severe pain). The average time to headache improvement (one point below the original intensity), to mild headache, and then to no headache is measured. An effective migraine treatment will reduce a headache symptom to mild or no headache by about 1.5 to 2 hours after administration.

Relief from any of the four symptoms require a drop from a score of >0 at time of report of onset of migraine attack (score of >1 for pain), to a score of ≤1 at the time point in question. However, freedom from pain (or other symptom) requires a reduction in grading of that symptom from an initial >0 result (score of >1 for pain) to 0 at the timepoint in question.

Functional disability (ability to perform usual daily activities) is measured with a 4 point scale as follows:
0=not at all impaired
1=slightly impaired
2=moderately impaired
3=severely or completely impaired There is a further question (How well did your Study Medication work?) at certain timepoints, where subjects are asked to evaluate the "global effectiveness" of their study medication using a 7 point categorical scale:
0=very much better
1=much better
2=a little better
3=no change
4=a little worse
5=much worse
6=very much worse In another aspect of the invention, methods of treating, preventing, or ameliorating one or more symptoms of migraine disease, conditions or disorders while at the same time avoiding the inducement of one or more drug-induced side effects are provided herein. In practicing such treatment methods, therapeutically effective amounts of the 8'-OH DHE compounds or compositions as described herein are administered to a subject in need of treatment using optimized 8'-OH DHE compositions (e.g., 8'-OH DHE derivatives) and/or dosage forms containing such compositions.

The subject methods involve administration of therapeutically effective amounts of the 8'-OH DHE compound, where the rate of administration does not result in one or more of drug-induced nausea, emesis, chest tightness and related cardiovascular effects such as blood pressure instability, venous and arterial constriction, or any other adverse effects known to be associated with treatment of migraine with commercially available DHE compounds or compositions.

In one aspect, the invention provides methods for providing an amount of the 8'-OH DHE compound to a subject at a selected rate sufficient to develop a circulating plasma concentration level of 8'-OH DHE effective for the 8'-OH DHE to act as an agonist against a serotonin receptor related to alleviating a migraine symptoms (wherein the 8'-OH DHE $C_{max}$ is attained within a time period ($T_{max}$) sufficient for providing partial relief from at least one migraine syndrome including but not limited to pain, nausea, phonophobia and photophobia, within a period of about 30, 60, 90, 120 or 180 minutes or less, or providing sustained relief for about 3, 6, 12, 18, 24 or 36 hours or more), while at the same time the 8'-OH DHE $C_{max}$ is kept low enough so as to remain insufficient for active binding of the 8'-OH DHE to an adrenergic or dopaminergic receptor to cause nausea and other unwanted drug-induced side effects. In this regard, 8'-OH DHE binding to an adrenergic or dopaminergic receptor will be insufficient to cause nausea and other drug-induced side effects when the 8'-OH DHE displays reduced (less than about 50%) or an absence of (about 20% or less) binding at dopaminergic receptors such as $D_{2L}$; and the 8'-OH DHE displays reduced (less than about 60%) or an absence of (about 20% or less) binding at adrenergic alpha$_{1A}$, alpha$_{1D}$, alpha$_{2c}$, alpha$_{2A}$ and alpha$_{2B}$ receptors. For example, the 8'-OH DHE composition can be administered at a rate such that the 8'-OH DHE $C_{max}$ is less than about 5,000; 7,500; 10,000; 15,000; 20,000; 25,000; 30,000; 40,000 or 50,000 pg/mL. In one particular example, the 8'-OH DHE composition is administered at a rate such that the 8'-OH DHE $C_{max}$ is less than about 4,500; 4,000; 3,500 or 3,000 pg/mL.

One particularly preferred method of carrying out such methods of the invention is to administer the 8'-OH DHE composition using oral pulmonary inhalation from a DPI or pMDI inhaler device. In one particular aspect of the invention, a pharmaceutically acceptable salt of the 8'-OH DHE compound is converted into crystalline particles using the supercritical fluid processes described in International Publication No. WO2005/025506A2 to provide a stable dry powder form of 8'-OH DHE that is suitable for use in a propellant suspension for administration via pulmonary aerosol inhalation. The 8'-OH DHE powder can be suspended in an HFA propellant such as HFA 134a (1,1,1,2-tetrafluoroethane) and HFA 227e (1,1,1,2,3,3,3-heptafluoropropane) and provided either alone or as a ratio of HFA propellants to match the density of the crystal 8'-OH DHE particles (a ratio selected to ensure that the final suspension avoids detrimental sedimentation or cream which can precipitate irreversible agglomeration, and instead promotes a loosely flocculated system), which is easily dispersed when shaken. The resulting 8'-OH DHE aerosol suspension can be contained in a suitable aerosol canister containing, preferably, a primeless valve that provides discrete 1 mg nominal doses of the 8'-OH DHE compound on each actuation (about 0.45-0.65 mg actual doses) from the canister, and the doses can be administered via oral pulmonary inhalation using a breath-actuated pMDI device such as the TEMPO® Inhaler (MAP Pharmaceuticals, Inc., Mountain View, Calif. 94043 USA).

In further related methods of the invention, 8'-OH DHE compound derivatives are provided wherein one or more positions on the ergoline ring and/or the peptide side chain have been substituted such that one or more hydrogen atoms of the specified group or radical are each, independently of one another, replaced with the same or different substituent including but not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, 8'-OH DHE compound derivatives are provided wherein one or more positions on the ergoline ring and/or the peptide side chain have been substituted such that one or more unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

The specific substitution or substitutions to the 8'-OH DHE compound in the resulting derivatives can provide for a reduction in a drug-induced side effect such as fibrosis, for example when the substitution or substitutions are suitable to reduce or eliminate agonism at the 5-HT$_{2B}$ receptor.

Also provided are methods for antagonizing receptors including 5-HT$_{2B}$ receptors and adrenergic alpha$_{1A}$, alpha$_{1D}$, alpha$_{2C}$, alpha$_{2A}$ and alpha$_{2B}$ receptors using the 8'-OH DHE compounds and compositions as described herein. In practicing the methods, therapeutically effective amounts of the compounds or compositions are administered.

Also provided are methods for agonizing the 5-HT$_{1D}$ and 5-HT$_{1B}$ receptors using the compounds and compositions described herein. In some aspects of the invention, methods of selectively agonizing the 5-HT$_{1D}$ receptor over the 5-HT$_{1B}$ receptor using the compounds and compositions described herein are provided.

In still other aspects of the invention, methods of reducing agonism of dopamine receptors when compared to agonism of dopamine receptors by other ergolines, such as, for example, DHE using the compounds and compositions described herein is provided below. In some embodiments, the dopamine receptor is the D$_{2L}$ receptor. In practicing the methods, therapeutically effective amounts of the compounds or compositions are administered.

The 8'-OH DHE compounds and compositions disclosed herein may also be used in the above-described methods in combination with one or more other active ingredients. In certain embodiments, the 8'-OH DHE compounds may be administered in combination, or sequentially, with another therapeutic agent. Such other therapeutic agents include those known for treatment, prevention, or amelioration of one or more symptoms associated with migraine.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the 8'-OH DHE compounds and compositions provided herein may be used with other agents to agonize and or antagonize the receptors mentioned above.

Finally, it should be noted that there are alternative ways of implementing the present invention. Accordingly, the present examples and aspects of the invention are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

Example 1

Hydroxylation of DHE to Give
8'-Hydroxy-Dihydroergotamine (8'-OH-DHE)

Bioconversion of the parent dihydroergotamine (DHE) molecule (the mesylate salt form) was carried out using *Rhodococcus* sp. AMRI-411 (Albany Molecular Research, Inc., Albany, N.Y.), a strain isolated from environmental samples used for biocatalysis screening. The AMRI-411 cells were grown according to the following protocol. Vials stored under liquid nitrogen vapor were thawed and approximately 1.0 mL of seed material was inoculated into 250 mL DeLong culture flasks containing 30 mL of Soybean Flour Glycerol Medium. Soybean Flour Glycerol Medium was composed of soy flour (5 g/L), yeast extract (5 g/L), NaCl (5 g/L), K$_2$HPO$_4$ (5 g/L) and glycerol (20 g/L) in deionized water. The pH was adjusted to 6.8 with 1 N HCl. The medium was autoclaved for 30 minutes at 16 psi and 122° C. and mixed prior to dispensing into flasks. This culture was grown at 28° C., 200 RPM with a 5 cm orbit for 24 hours. The resulting culture was used to inoculate a 250 mL DeLong culture flask containing 30 mL Soybean Flour Glycerol Medium at 10% (v/v). This second culture was grown at 28° C., 100 RPM with a 5 cm orbit for an additional 24 hours. Cells from this culture were recovered via centrifugation at 4,000×g for 5 minutes. These cells were subsequently resuspended in an equal volume of 0.22 micron filter sterilized 100 mM potassium phosphate buffer, pH 7.4, supplemented with 10 g/L dextrose and returned to the same incubation conditions with 200 RPM shaking.

Bioconversions were initiated by the addition of DHE mesylate to the AMRI-411 suspensions to give a 0.25 mg/mL final concentration. These additions were made from a 25 mg/mL stock solution of DHE dissolved in methanol. Bioconversions were allowed to proceed for 24 hours under the same incubation conditions. At the conclusion of the bioconversion, an equal volume of ethyl acetate was added and the mixture stirred with an overhead mixer. Upon phase separation, the ethyl acetate was collected, dried over sodium sulfate, and removed by evaporation.

Solids were dissolved in methanol, and 8'-OH DHE was isolated via preparatory HPLC. Pure fractions containing a single epimer of the 8'-OH DHE compound were pooled, the acetonitrile was evaporated, and the remaining aqueous portion was lyophilized. Overall isolated biotransformation yields were approximately 20%.

Example 2

Determination of Association/Dissociation Constants
on Human D$_{2L}$, 5-HT$_{1A}$, 5-HT$_{1B}$, 5-HT$_{1D}$ and
5-HT$_{2B}$ Receptors Determination of association ($k_{on}$)/dissociation ($k_{off}$) constants for 8'-OH DHE and the parent DHE molecule (compared against sumatriptan) on human D$_{2L}$, 5-HT$_{1A}$, 5-HT$_{1B}$, 5-HT$_{1D}$ and 5-HT$_{2B}$ receptors was carried out using the following radioligand binding assay.

Compounds: the 8'-OH DHE and DHE compounds were in powder form and stored at room temperature (RT) prior to testing. For the testing, the compounds were prepared according to Table 1 below.

TABLE 1

| | Solvent | Compound | Storage |
|---|---|---|---|
| Master Solution | 100% DMSO | 10 mM | −20° C. |
| Intermediate dilution for all compounds on 5-HT$_{1A}$, 5-HT$_{1B}$ and 5-HT$_{1D}$ receptors and test compounds on 5-HT$_{2B}$ receptor. | 100% DMSO | 2 mM-2 nM | Max 4 hours at RT |
| Assay plate for all compounds on 5-HT$_{1A}$, 5-HT$_{1B}$ and 5-HT$_{1D}$ receptors and test compounds on 5-HT$_{2B}$ receptor. | Assay buffer | 20 μM-20 pM | Max 4 hours at RT |
| Intermediate dilution for all compounds on D$_{2L}$ receptor and sumatriptan on 5-HT$_{2B}$ receptor. | 100% DMSO | 10 mM-200 nM | Max 4 hours at RT |

TABLE 1-continued

|  | Solvent | Compound | Storage |
|---|---|---|---|
| Assay plate for all compounds on $D_{2L}$ receptor and sumatriptan on 5-$HT_{2B}$ receptor. | Assay buffer | 100 μM-2 nM | Max 4 hours at RT |

For kinetics of radioligand competitive binding, serial dilutions were performed from master solution in 100% DMSO to obtain intermediate concentrations 200-fold higher than the concentrations to be tested. Each test sample was diluted 100-fold in the assay buffer and dispensed into the test plate.

The radioligand binding experiments were conducted with Euroscreen membrane preparations as set forth in Table 2 below.

TABLE 2

| Receptor | Accession No. | Cell Background | Radioligand | Reference Compound |
|---|---|---|---|---|
| $D_{2L}$ | AABB26819.1 | CHO-K1 | [$^3$H]-Spiperone | Risperidone |
| 5-$HT_{1A}$ | NP_000515.2 |  | [$^3$H]-WAY100635 | Methiothepin |
| 5-$HT_{1B}$ | NP_000854.1 |  | [$^3$H]-CT | 5-CT |
| $HT_{1D}$ | NP_000855.1 |  | [$^3$H]-CT | 5-HT |
| 5-$HT_{2B}$ | NP_000858.2 |  | [$^3$H]-Mesulergine | 5-HT |

The materials used in the radioligand binding experiments were as follows:

$D_{2L}$ Radioligand Binding Assay
Assay buffer: 25 mM HEPES (pH 7.4), 5 mM $MgCl_2$, 1 mM $CaCl_2$, BSA protease free 0.5%
Washing buffer: 25 mM HEPES (pH 7.4), 5 mM $MgCl_2$, 1 mM $CaCl_2$
Membrane: recombinant CHO-K1-$D_{2L}$ membranes thawed on ice and diluted in assay buffer (2 μg/well)
Ligand: Risperidone (Tocris Bioscience, 2865)
Radioligand: [$^3$H]-Spiperone (TRK818, diluted in assay buffer for a final concentration of 3 nM)
Filter plate: GF/B Unifilter plate (Perkin Elmer, 6005177) presoaked in 0.5% PEI for 2 hours at RT.

5-$HT_{1A}$ Radioligand Binding Assay
Assay buffer: 50 mM Tris (pH 7.4), 4 mM $CaCl_2$, 0.1% ascorbic acid, 10 μg/mL saponin
Washing buffer: 50 mM Tris (pH 7.4)
Membrane: recombinant CHO-K1-5-$HT_{1A}$ membranes thawed on ice and diluted in assay buffer (10 μg/well)
Ligand: Methiothepin mesylate (Sigma, M-149)
Radioligand: [$^3$H]-WAY100635 (Perkin Elmer, NET1164, diluted in assay buffer for a final concentration of 1 nM)
Filter plate: GF/C Unifilter plate (Perkin Elmer, 6005174) presoaked in 0.5% Brij for 2 hours at RT.

5-$HT_{1B}$ Radioligand Binding Assay
Assay buffer: 50 mM Tris (pH 7.4), 12.5 mM $MgCl_2$, 0.1% ascorbic acid, 1 mM EDTA
Washing buffer: 50 mM Tris (pH 7.4)
Membrane: recombinant CHO-K1-5-$HT_{1B}$ membranes thawed on ice and diluted in assay buffer (7 μg/well)
Ligand: 5-CT (Tocris, 0458)
Radioligand: [$^3$H]-CT (Perkin Elmer, TRK1038, diluted in assay buffer for a final concentration of 0.6 nM)
Filter plate: GF/B Unifilter plate (Perkin Elmer, 6005177) presoaked in 0.5% PEI for 2 hours at RT.

5-$HT_{1D}$ Radioligand Binding Assay
Assay buffer: 50 mM Tris (pH 7.4), 4 mM $CaCl_2$, 0.1% ascorbic acid
Washing buffer: 50 mM Tris (pH 7.4)
Membrane: recombinant CHO-K1-5-$HT_{1D}$ membranes thawed on ice and diluted in assay buffer (10 μg/well)
Ligand: 5-HT (Sigma, H-9523)
Radioligand: [$^3$H]-CT (Perkin Elmer, TRK1038, diluted in assay buffer for a final concentration of 0.5 nM)
Filter plate: GF/B Unifilter plate (Perkin Elmer, 6005177) presoaked in 0.5% PEI for 2 hours at RT.

5-$HT_{2B}$ Radioligand Binding Assay
Assay buffer: 50 mM Tris (pH 7.4), 4 mM $CaCl_2$, 0.1% ascorbic acid
Washing buffer: 50 mM Tris (pH 7.4)
Membrane: recombinant CHO-K1-5-$HT_{2B}$ membranes thawed on ice and diluted in assay buffer (7 μg/well)
Ligand: 5-HT (Sigma, H-9523)
Radioligand: [$^3$H]-Mesulergine (Perkin Elmer, TRK845, diluted in assay buffer for a final concentration of 1 nM)
Filter plate: GF/B Unifilter plate (Perkin Elmer, 6005177) presoaked in 0.5% PEI for 2 hours at RT.

Determination of the $K_{on}$ constant. Radioligand association kinetics on each receptor were performed by adding in the wells of a 96 well plate 50 μL of radioligand and 50 μL of membrane extracts. The samples were incubated for the times reported in Table 3 below at a temperature optimized for each receptor and filtered over a filter plate. After washing the filters 5 times with 0.5 mL of ice-cold washing buffer, 50 μL of Microscint 20 (Packard) were added to the filters and the plates were incubated 15 min on an orbital shaker and then counted for 1 min/well. This allowed determination of the $k_{obs}$ for each radioligand. Association kinetics were performed at 5 different radioligand concentrations optimized for each receptor (see Table 3 below) to determine 5 different $k_{obs}$. The different $k_{obs}$ were then plotted against the [radioligand] and the $K_{on}$ was calculated using the following equation: $k_{on} = -k_{off}/[radioligand]$.

TABLE 3

| Receptor | [RL] (nM) | Time-points (min) | | | | | | | | | |
|---|---|---|---|---|---|---|---|---|---|---|---|
| 5-$HT_{1A}$ | 1 | 0.5 | 2 | 5 | 10 | 15 | 20 | 25 | 30 | 45 | 60 |
|  | 2, 3, 4, 5 | 0.5 | 1 | 2 | 3 | 5 | 7 | 10 | 15 | 25 | 45 |
| 5-$HT_{1B}$ | 0.6 | 0.5 | 1 | 1.5 | 2 | 2.5 | 3 | 3.5 | 4 | 4.5 | 5 |
|  | 1, 2, 5, 7.5 | 0.25 | 0.5 | 0.75 | 1 | 1.5 | 2 | 2.5 | 3 | 4 | 5 |
| 5-$HT_{1D}$ | 1, 2.5, 3.75, 5, 7.5 | 0.25 | 0.5 | 0.75 | 1 | 1.5 | 2 | 2.5 | 3 | 4 | 5 |
| 5-$HT_{2B}$ | 1 | 0.5 | 2 | 5 | 10 | 15 | 20 | 25 | 30 | 45 | 60 |
|  | 2, 5, 10, 15 | 1 | 2 | 5 | 7 | 10 | 20 | 30 | 45 | 60 | 90 |
| $D_{2L}$ | 3.5 | 0.17 | 0.33 | 0.5 | 0.67 | 0.83 | 1 | 1.2 | 1.5 | 2 | 5 |
|  | 1, 2, 3, 5 | 0.17 | 0.33 | 0.5 | 0.67 | 0.83 | 1 | 1.5 | 2 | 3 | 5 |

Determination of the $K_{off}$ constant. Radioligand dissociation kinetics on each receptor were performed by adding in the wells of a 96 well plate 45 μL of radioligand and 45 μL of membrane extracts. The samples were incubated as reported in Table 4 below at a temperature optimized for each receptor until binding equilibrium was reached as determined by the association kinetics experiment. Then, 10 μL of cold competitor (reference ligand) were added at a 200 fold excess (final concentration) for the times reported in Table 4 at the optimized temperature. The samples were then filtered over a filter plate. After washing the filters 5 times with 0.5 mL of ice-cold washing buffer, 50 μL of Microscint 20 (Packard) were added to the filters and the plates were incubated 15 min on an orbital shaker and then counted for 1 min/well. This allowed determination of the $k_{off}$ for each radioligand.

TABLE 4

| Receptor | Time-points (min) | | | | | | | | | |
|---|---|---|---|---|---|---|---|---|---|---|
| $5\text{-}HT_{1A}$ | 10 | 30 | 60 | 100 | 150 | 200 | 250 | 300 | 350 | 400 |
| $5\text{-}HT_{1B}$ | 1 | 2 | 3 | 4 | 5 | 10 | 15 | 20 | 25 | 30 |

TABLE 4-continued

| Receptor | Time-points (min) | | | | | | | | | |
|---|---|---|---|---|---|---|---|---|---|---|
| $5\text{-}HT_{1D}$ | 1 | 2 | 3 | 4 | 5 | 10 | 15 | 20 | 25 | 30 |
| $5\text{-}HT_{2B}$ | 1 | 2 | 5 | 10 | 15 | 20 | 30 | 45 | 60 | 120 |
| $D_{2L}$ | 10 | 30 | 60 | 100 | 150 | 200 | 250 | 300 | 350 | 400 |

Determination of $IC_{50}$ and $K_i$ constant for each test compound. Radioligand competition binding on each receptor were performed by adding in the wells of a 96 well plate 50 μL of test compound at increasing concentration as reported in Table 5 below, 25 μL of radioligand and 25 μL of membrane extracts. The samples were incubated for 60 min (or 4 hours for a second experiment on 5-HT2B receptors) at a temperature optimized for each receptor and then filtered over a filter plate. After washing the filters 5 times with 0.5 mL of ice-cold washing buffer, 50 μL of Microscint 20 (Packard) were added to the filters and the plates were incubated 15 min on an orbital shaker and then counted for 1 min/well. The test compounds were tested in duplicate at the nanomolar concentrations reported below in Table 5.

TABLE 5

| Cpds/Receptors | Concentration range (nM) | | | | | | | | | |
|---|---|---|---|---|---|---|---|---|---|---|
| All cpds on $5\text{-}HT_{1A}$ | 0.01 | 0.1 | 1 | 3 | 10 | 30 | 100 | 300 | 1,000 | 10,000 |
| All cpds on $5\text{-}HT_{1B}$ | 0.01 | 0.1 | 1 | 3 | 10 | 30 | 100 | 300 | 1,000 | 10,000 |
| All cpds on $5\text{-}HT_{1D}$ | 0.01 | 0.1 | 1 | 3 | 10 | 30 | 100 | 300 | 1,000 | 10,000 |
| Sumatriptan on $5\text{-}HT_{2B}$ | 1 | 10 | 30 | 100 | 300 | 1,000 | 3,000 | 10,000 | 25,000 | 50,000 |
| All cpds on $D_{2L}$ | 1 | 10 | 30 | 100 | 300 | 1,000 | 3,000 | 10,000 | 25,000 | 50,000 |

Determination of $k_{on}$ and $k_{off}$ constants for each test compound. Each compound was first assessed in a pilot experiment to evaluate its effect on the kinetic binding of each receptor-radioligand pair. These pilot experiments were performed at on compound concentration and were composed of 10 time-points measurements in duplicate (2, 5, 10, 20, 30, 45, 60, 90, 120 and 150 minutes). Radioligand binding competition kinetics on each receptor were performed by adding in the wells of a 96 well plate 50 μL test compound at increasing concentrations (final concentration 0.3-, 1- and 3-times the $IC_{50}$), 25 μL of radioligand and 25 μL of membrane extracts. The samples were incubated at a temperature optimized for each receptor for different times (20 time points were selected according to the pilot experiment as reported in Table 6 below) and filtered over a filter plate. After washing the filters 5 times with 0.5 mL of ice-cold washing buffer, 50 μL of Microscint 20 (Packard) were added to the filters and the plates were incubated 15 min on an orbital shaker and then counted for 1 min/well. This allowed the determination of the association ($k_{on}$) and dissociation ($k_{off}$) constants for binding of the compounds to each receptor using the "Kinetics of competitive binding" nonlinear regression of the Prism 4 software (GraphPad Software, Inc.).

TABLE 6

| Cpds/Receptors | Time-points (min) | | | | | | | | | | | | | | | | | | | |
|---|---|---|---|---|---|---|---|---|---|---|---|---|---|---|---|---|---|---|---|---|
| All cpds on $5\text{-}HT_{1A}$ | 1 | 2 | 3 | 5 | 7 | 10 | 15 | 20 | 25 | 30 | 35 | 40 | 50 | 60 | 70 | 90 | 120 | 150 | 180 | 210 |
| All cpds on $5\text{-}HT_{1B}$ | 1 | 2 | 3 | 5 | 7.5 | 10 | 12.5 | 15 | 17.5 | 20 | 25 | 30 | 35 | 40 | 45 | 50 | 60 | 70 | 90 | 120 |

TABLE 6-continued

| Cpds/Receptors | | | | | | | | Time-points (min) | | | | | | | | | | | |
|---|---|---|---|---|---|---|---|---|---|---|---|---|---|---|---|---|---|---|---|
| All cpds on 5-HT$_{1D}$ | 1 | 2 | 3 | 4 | 6 | 8 | 10 | 15 | 20 | 25 | 30 | 35 | 40 | 50 | 60 | 70 | 80 | 100 | 120 | 150 |
| Sumatriptan on 5-HT$_{2B}$ | 1 | 2 | 3 | 4 | 5 | 7 | 10 | 12.5 | 15 | 17.5 | 20 | 25 | 30 | 40 | 50 | 60 | 70 | 90 | 120 | 150 |
| All cpds on D$_{2L}$ | 1 | 2 | 3 | 4 | 5 | 7 | 10 | 12.5 | 15 | 17.5 | 20 | 25 | 30 | 40 | 50 | 60 | 70 | 90 | 120 | 150 |

The results of the association ($k_{on}$)/dissociation ($k_{off}$) constants for 8'-OH DHE and the parent DHE molecule (compared against sumatriptan) on human D$_{2L}$, 5-HT$_{1A}$, 5-HT$_{1B}$, 5-HT$_{1D}$ and 5-HT$_{2B}$ receptors are reported in Table 7 below.

TABLE 7

| Receptor | Compound | IC$_{50}$ from binding assay (nM) | Avg K$_{off}$ (min−1) | Avg Dissociation half-life (hr) |
|---|---|---|---|---|
| 5-HT$_{1D}$ | Sumatriptan | 6.55 | 0.1315 | 0.09 |
| | DHE | 0.65 | 0.0090 | 1.28 |
| | 8'-OH DHE | 0.80 | 0.0105 | 1.10 |
| 5-HT$_{1B}$ | Sumatriptan | 7.63 | 0.0673 | 0.17 |
| | DHE | 0.55 | 0.0084 | 1.38 |
| | 8'-OH DHE | 0.77 | 0.0059 | 1.94 |
| D$_{2L}$ | Sumatriptan | n/a | n/a | n/a |
| | DHE0.77 | 231.33 | 0.0475 | 0.24 |
| | 8'-OH DHE | 297.36 | 0.0763 | 0.15 |
| 5-HT$_{1A}$ | Sumatriptan | 778.39 | 0.0106 | 1.09 |
| | DHE | 0.27 | −0.0008 | −14.49 |
| | 8'-OH DHE | 0.43 | −0.0008 | −14.35 |
| 5-HT$_{2B}$ | Sumatriptan | 19859.00 | 0.0311 | 0.37 |
| | DHE | 12.92 | −0.0023 | −5.09 |
| | 8'-OH DHE | 7.73 | −0.0015 | −7.55 |

Example 3

Determination of Agonist and Antagonist Activities on Human Adrenergic α$_{1D}$, Dopamine D$_{2L}$, and Serotonin 5-HT$_{1B}$, 5-HT$_{1D}$, 5-HT$_{1F}$, 5-HT$_3$, 5-HT$_{4e}$, and 5-HT$_{5A}$ Receptors Functional profiling of agonist and antagonist activities of 8'-OH DHE on human Adrenergic α$_{1D}$, Dopamine D$_{2L}$, and Serotonin 5-HT$_{1B}$, 5-HT$_{1D}$, 5-HT$_{1F}$, 5-HT$_3$, 5-HT$_{4e}$ and 5-HT$_{5A}$ receptors (compared against the parent (DHE) molecule) was carried out as follows.

Compounds: the 8'-OH DHE and DHE test compounds were in powder form and stored at 4° C. (DHE) or −20° C. (8'-OH DHE) prior to testing. For the testing, the compounds were prepared according to Tables 8 and 9 below.

TABLE 8

(Dose-Response Curves)

| | Solvent | Compound | Storage |
|---|---|---|---|
| Master Solution | 100% DMSO | 10 mM | −20° C. |
| Intermediate dilution for Aequorin and cAMP HTRF assays. | 100% DMSO | 4 mM-2.048 nM | Max 4 hours at RT |
| Assay plate for Aequorin and cAMP HTRF assays | Assay buffer | 40 μM-20.48 pM | Max 4 hours at RT |
| Intermediate dilution for GTPγS assay. | 100% DMSO | 2 mM-1.024 nM | Max 4 hours at RT |
| Assay plate for GTPγS assay. | Assay buffer | 20 μM-10.42 nM | Max 4 hours at RT |

TABLE 9

(Single Point Conc. of Cmpds)

| Compound | Master Solution | Assay Type | Intermediate dilution (100% DMSO) | Assay plate conc. (assay buffer) |
|---|---|---|---|---|
| DHE | 10 mM | Aeq | 1 mM | 206 nM |
| | | | 10 μM | 23.4 nM |
| | | | | 12.5 nM |
| | | | | 8.74 nM |
| | | | 1 μM | 0.440 nM |
| | | | | 0.268 nM |
| | | cAMP | 100 μM | 412 nM |
| | | | | 46.8 nM |
| | | | | 25 nM |
| | | | | 17.5 nM |
| | | | 10 μM | 0.88 nM |
| | | | | 0.536 nM |
| 8'-OH DHE | 10 mM | Aeq/GTP | 1 μM | 1.07 nM |
| | | | | 0.5 nM |
| | | | | 0.38 nM |
| | | | | 0.2 nM |
| | | | | 0.09 nM |
| | | | | 0.0834 nM |
| | | cAMP | 10 μM | 2.14 nM |
| | | | 1 μM | 1 nM |
| | | | | 0.76 nM |
| | | | | 0.4 nM |
| | | | | 0.18 nM |
| | | | | 0.167 nM |

The SPA 35S-GTPγS tests were conducted with Euroscreen membrane preparations using Aequorin assays and cAMP. The HTRF assays were conducted with recombinant cell lines. The receptor accession numbers, cellular background and reference compounds are as reported below in Table 10.

TABLE 10

| Receptor | Accession No. | Cell line | Reference agonist | Reference antagonist |
|---|---|---|---|---|
| Adrenergic $\alpha_{1D}$ | NP_000669.1 | CHO-K1 mit Aeq | Cirazoline | Quinazoline |
| Dopamine $D_{2L}$ | AAB26819.1 | CHO-K1 | Quinpirol | Haloperidol |
| Serotonin 5-$HT_{1B}$ | NP_000854.1 | CHO-K1 | 5-CT | Methiothepin |
| Serotonin 5-$HT_{1D}$ | NP_000855.1 | CHO-K1 | 5-CT | (not validated) |
| Serotonin 5-$HT_{1F}$ | NP_000857.1 | CHO-K1 | 5-HT or LY334370 | Methysergide |
| Serotonin 5-$HT_3$ | NP_000860.2 | HEK-293-mit Aeq | 5-HT | MDL72222 |
| Serotonin 5-$HT_{4e}$ | NP_955525.1 | Transient CHO-K1 | 5-HT | GR113808 |
| Serotonin 5-$HT_{5A}$ | NP_076917 | CHO-K1 mit Aeq-$G_{\alpha 16}$ | 5-CT | Methiothepin |

The test specifications were as follows:
(1) DHE and 8'-OH DHE were tested for agonist and antagonist activity at the human Adrenergic $\alpha_{1D}$, Serotonin 5-$HT_3$ and Serotonin 5-$HT_{5A}$ receptors using aequorin assay (in triplicate) at the following nanomolar concentrations:

| Agonist | 0.01024 | 0.0512 | 0.256 | 1.28 | 6.4 | 32 | 160 | 800 | 4,000 | 20,000 |
|---|---|---|---|---|---|---|---|---|---|---|
| Antagonist | 0.00512 | 0.0256 | 0.128 | 0.64 | 3.2 | 16 | 80 | 400 | 2,000 | 10,000 |

(2) DHE and 8'-OH DHE were tested for agonist and antagonist activity at the human Dopamine $D_{2L}$ receptor using cAMP HTRF assay (in triplicate) at the following nanomolar concentrations:

| .00512 | 0.0256 | 0.128 | 0.64 | 3.2 | 16 | 80 | 400 | 2,000 | 10,000 |
|---|---|---|---|---|---|---|---|---|---|

(3) 8'-OH DHE was tested for agonist and antagonist activity at the human Serotonin 5-$HT_{1B}$ and Serotonin 5-$HT_{1D}$ receptors using GTPγS assay (in triplicate) at the following nanomolar concentrations:

| 0.00512 | 0.0256 | 0.128 | 0.64 | 3.2 | 16 | 80 | 400 | 2,000 | 10,000 |
|---|---|---|---|---|---|---|---|---|---|

(4) DHE and 8'-OH DHE were tested for agonist and antagonist activity at the human Serotonin 5-$HT_{1F}$ and Serotonin 5-$HT_{4E}$ receptors using cAMP HTRF assay (in triplicate) at the following nanomolar concentrations:

| 0.00512 | 0.0256 | 0.128 | 0.64 | 3.2 | 16 | 80 | 400 | 2,000 | 10,000 |
|---|---|---|---|---|---|---|---|---|---|

(5) DHE was tested for agonist and antagonist activity at the human Adrenergic $\alpha_{1D}$, Serotonin 5-$HT_3$ and Serotonin 5-$HT_{5A}$ receptors using aequorin assay (in triplicate), and at the human Dopamine $D_{2L}$, Serotonin 5-$HT_{1F}$ and Serotonin 5-$HT_{4E}$ receptors using cAMP HTRF assay (in triplicate) at the following nanomolar concentrations:

| 6.25 | 4.37 | 11.7 | 0.22 | 0.134 | 103 |
|---|---|---|---|---|---|

(6) 8'-OH DHE was tested for agonist and antagonist activity at the human Adrenergic $\alpha_{1D}$, Serotonin 5-$HT_3$ and Serotonin 5-$HT_{5A}$ receptors using aequorin assay (in triplicate), at the human Dopamine $D_{2L}$, Serotonin 5-$HT_{1F}$ and Serotonin 5-$HT_{4E}$ receptors using cAMP HTRF assay (in triplicate), and at the human Serotonin 5-$HT_{1B}$ and Serotonin 5-$HT_{1D}$ receptors using GTPγS assay (in triplicate) at the following nanomolar concentrations:

| 0.25 | 0.1 | 0.19 | 0.045 | 0.0417 | 0.534 |
|---|---|---|---|---|---|

The assay methods were carried out as follows.

(Aequorin Assay)

CHO-K1 or HEK-293 cells coexpressing mitochondrial apoaequorin and recombinant human Adrenergic $\alpha_{1D}$ receptor, or recombinant human Serotonin 5-$HT_3$ receptor, or recombinant human Serotonin 5-$HT_{5A}$ receptor grown to mid-log phase in culture media without antibiotics were detached with PBS-EDTA, centrifuged and resuspended in assay buffer (DMEM/HAM's F12 with HEPES, without phenol red+0.1% BSA protease free) at a concentration of $1\times10^6$ cells/mL. Cells were incubated at RT for at least 4 hours with coelenterazine h. The reference agonist was tested to evaluate performance of the assay on each day of the test and to determine $EC_{50}$. For agonist testing, 50 μL of cell suspension was mixed with 50 μL of test compound or reference agonist in a 96-well plate. The resulting emission of light was recorded using Hamamatsu Functional Drug Screening System 6000 (FDSS 6000 luminometer). For antagonist testing, 100 μL of the reference agonist at its $EC_{80}$ was injected on the mix of cells and test compounds, following an incubation of 15 minutes after the first injection. The resulting emission of light was recorded using the FDSS 6000 luminometer. To standardize the emission of recorded light (determination of the '100% signal') across plates and across different experiments, some of the wells contained 100 μM digitonin or a saturating concentration of ATP (20 μM).

(cAMP HTRF Assay for 5-$HT_{4E}$ Receptor)

CHO-K1 cells were transiently transfected with human recombinant Serotonin 5-$HT_{4e}$ receptor. Two days after transfection, cells were detached by gentle flushing with PBS-EDTA (5 mM EDTA), recovered by centrifugation and resuspended in assay buffer (KRH: 5 mM KCl, 1.25 mM $MgSO_4$, 124 mM NaCl, 25 mM HEPES, 13.3 mM Glucose, 1.25 $KH_2PO_4$, 1.45 mM $CaCl_2$, and 0.5 g/L BSA). Dose response curves were performed in parallel with the reference compounds. For the agonist test (96 well), 12 μL of cells were mixed with 6 μl, of the test compound at increasing concentrations and 6 μL, of assay buffer, and then incubated for 30 minutes at RT. After addition of the lysis buffer and 1 hour incubation, cAMP concentrations were estimated according to manufacturer's specification (from the HTRF kit). For the antagonist test (96 well), 12 μL of cells were mixed with 6 μL of the test compound at increasing concentrations and then incubated for 10 minutes. Thereafter, 6 µL of the reference agonist was added at a final concentration corresponding to the historical $EC_{80}$. The plates were then incubated for 30 minutes at RT. After addition of the lysis buffer and 1 hour incubation, cAMP concentrations were estimated according to manufacturer's specification (from the HTRF kit).

(cAMP HTRF Assay for $D_{2L}$ and 5-$HT_{1F}$ Receptors).

CHO-K1 cells expressing recombinant Dopamine $D_{2L}$ receptor or Serotonin 5-$HT_{1F}$ receptor grown prior to the test in media without antibiotic were detached by gentle flushing with PBS-EDTA (5 mM EDTA), recovered by centrifugation and resuspended in assay buffer (KRH: 5 mM KCl, 1.25 mM $MgSO_4$, 124 mM NaCl, 25 mM HEPES, 13.3 mM Glucose, 1.25 $KH_2PO_4$, 1.45 mM $CaCl_2$, and 0.5 g/L BSA). Dose response curves were performed in parallel with the reference compounds. For the agonist test (96 well), 12 µl of cells were mixed with 6 µL of the test compound at increasing concentrations and 6 µL of forskolin then incubated for 30 minutes at RT. After addition of the lysis buffer and 1 hour incubation, cAMP concentrations were estimated according to manufacturer's specification (from the HTRF kit). For the Antagonist test (96 well) 12 µL of cells were mixed with 6 µL of the test compound at increasing concentrations and then incubated for 10 minutes. Thereafter, 6 µL of a mixture of the forskolin and reference agonist was added at a final concentration of agonist corresponding to the historical $EC_{80}$. The plates were then incubated for 30 minutes at RT. After addition of the lysis buffer and 1 hour incubation, cAMP concentrations were estimated according to manufacturer's specification (from the HTRF kit).

(GTPγS Functional Assay for 5-$HT_{1B}$ Receptor).

The materials used in this test were as follows.

Assay buffer: 20 mM HEPES pH 7.4; 100 mM NaCl; 10 µg/mL saponin; 3 mM $MgCl_2$;

Membranes: recombinant 5-$HT_{1B}$ membrane extracts thawed on ice and diluted in assay buffer to give 500 µg/mL (5 µg/10 µL) and kept on ice;

GDP: diluted in assay buffer to give 30 µM solution (3 µM final concentration);

Beads mg/mL: PVT-WGA (Perkin Elmer, RPNQ001), diluted in assay buffer at 100 (0.5 mg/µL);

GTPγS: (Perkin Elmer NEG030X), diluted in assay buffer to give 0.1 nM final conc.;

Ligand: 5-CT (Tocris, 458), diluted in assay buffer.

The assay procedure was carried out as follows. Membranes were mixed with GDP (v/v) and incubated for at least 15 minutes on ice. In parallel, GTPγ[$^{35}$S] was mixed with the beads (v/v) just before starting the reaction. The following reagents were successively added in the wells of an Optiplate (Perkin Elmer): 50 µL of test compound; 20 µL of the membranes:GDP mixture; 10 µL of assay buffer (for agonist testing); and 20 µL of the GTPγ[$^{35}$S]:beads mixture. The plates were covered with a top seal, shaken on an orbital shaker for 2 minutes, and then incubated for 30 minutes at RT. The plates were then centrifuged for 10 minutes at 2,000 rpm and counted for 1 min/well with a Perkin Elmer TopCount reader.

(GTPγS Functional Assay for 5-$HT_{1D}$ Receptor).

The materials used in this test were as follows.

Assay buffer: 20 mM HEPES pH 7.4; 100 mM NaCl; 10 µg/mL saponin; 3 mM $MgCl_2$;

Membranes: recombinant 5-$HT_{1D}$ membrane extracts thawed on ice and diluted in assay buffer to give 500 µg/mL (5 µg/10 µL) and kept on ice;

GDP: diluted in assay buffer to give 30 µM solution (3 nM final concentration);

Beads mg/mL: PVT-WGA (Perkin Elmer, RPNQ001), diluted in assay buffer at 100 (0.5 mg/4);

GTPγS: (Perkin Elmer NEG030X), diluted in assay buffer to give 0.1 nM final conc.;

Ligand: 5-CT (Tocris, 458), diluted in assay buffer.

The assay procedure was carried out as follows. Membranes were mixed with GDP (v/v) and incubated for at least 15 minutes on ice. In parallel, GTPγ[$^{35}$S] was mixed with the beads (v/v) just before starting the reaction. The following reagents were successively added in the wells of an Optiplate (Perkin Elmer): 50 µL of test compound; 20 µL of the membranes:GDP mixture; 10 µL of assay buffer (for agonist testing); and 20 µL of the GTPγ[$^{35}$S]:beads mixture. The plates were covered with a top seal, shaken on an orbital shaker for 2 minutes, and then incubated for 30 minutes at RT. The plates were then centrifuged for 10 minutes at 2,000 rpm and counted for 1 min/well with a Perkin Elmer TopCount reader.

Results:

Agonist activity of the test compounds was expressed as a percentage of the activity of the reference agonist at its $EC_{100}$ concentration. Antagonist activity of the test compounds was expressed as a percentage of the inhibition of the reference agonist activity at its $EC_{80}$ concentration. Dose-response data from the test compounds were analyzed with XLfit (IDBS) software using nonlinear regression applied to a sigmoidal dose-response model and the following equation:

XL Fit fit Model 203: 4 Parameter Logistic Model, where
A: Bottom
B: TOP
C: Log $EC_{50}$
D: Hill $$Fit = (A + ((B-A)/(1+(((10^C)/x)^D))))$$

$$Inv = ((10^C)/((((b-A)/(y-A))-1)^(1/D)))$$

$$Res = (y - fit).$$

The results of the functional profiling of agonist and antagonist activities of 8'-OH DHE on human Adrenergic $\alpha_{1D}$, Dopamine $D_{2L}$, and Serotonin 5-$HT_{1B}$, 5-$HT_{1D}$, 5-$HT_{1F}$, 5-$HT_3$, 5-$HT_{4e}$ and 5-$HT_{5A}$ receptors (compared against the parent (DHE) molecule) are reported below in Table 11.

TABLE 11

| | Compounds | |
|---|---|---|
| Receptors | 8'-OH DHE | DHE |
| Adrenergic $\alpha_{1D}$ | 0.61 (antagonist) | 1.32 (antagonist) |
| Dopamine $D_{2L}$ | 1.61 (agonist) | 0.835 (agonist) |
| Serotonin 5-$HT_{1B}$ | 0.73 (agonist) | — |
| Serotonin 5-$HT_{1D}$ | 0.49 (agonist) | — |
| Serotonin 5-$HT_{1F}$ | inactive | inactive |
| Serotonin 5-$HT_3$ | >10,000 (antagonist) | 3855 (antagonist) |
| Serotonin 5-$HT_{4e}$ | 109 (agonist) | 105 (agonist) |
| Serotonin 5-$HT_{5A}$ | 73.3 (antagonist) | 48.8 (antagonist) |

Example 4 pMDI Composition Containing 8'-OH Compound 79.4 mg of 8'-OH DHE mesylate is dispersed in a 5 mL composition, consisting of a mixture of HFA 134a (1,1,1,2-tetrafluoroethane) and HFA 227ea (1,1,1,2,3,3,3-heptafluoropropane ranging from 0-100% HFA 227ea. The resulting suspension is filled using Pamasol filling equipment into aluminum aerosol canisters through a pharmaceutically acceptable 63 µL metering valve.

Example 5 pMDI Composition Containing 8'-OH Compound with PEG 127 mg 8'-OH DHE mesylate is dispersed in an 8 mL composition, consisting of a mixture of 25% HFA 134a (1,1,1,2-tetrafluoroethane) and 75% HFA 227ea (1,1,1,2,3,3,3-heptafluoropropane and containing 0.1% w/v PEG 1000 as a suspension stabilizing agent. When tested for aerosol particle size distribution using a next generation Impactor (NGI) at 60 Lmin$^{-1}$, fine particles fraction (% of emitted dose <5 µm vs. emitted dose) is anticipated to be >15%.

Example 6 pMDI Composition Containing 8'-OH Compound with Soy Lecithin 119 mg 8'-OH DHE mesylate is dispersed in an 5 mL composition, consisting of a mixture of 33% HFA 134a (1,1,1,2-tetrafluoroethane) and 67% HFA 227ea (1,1,1,2,3,3,3-heptafluoropropane and containing 0.01% w/v hydrogenated soy lecithin as a suspension stabilizing agent. When tested for aerosol particle size distribution using a next generation Impactor (NGI) at 60 Lmin$^{-1}$, fine particles fraction (% of emitted dose <5 µm vs. emitted dose) is anticipated to be >15%.

Example 7 pMDI Composition Containing 8'-OH Compound with Oleic Acid 79.4 mg 8'-OH DHE mesylate, dissolved in an 5 mL composition, consisting of a mixture of 33% HFA 134a (1,1,1,2-tetrafluoroethane) and 67% HFA 227ea (1,1,1,2,3,3,3-heptafluoropropane and containing 0.2% w/v oleic acid as a suspension stabilizing agent and 5% w/v ethanol. When tested for aerosol particle size distribution using a next generation Impactor (NGI) at 60 Lmin$^{-1}$, fine particles fraction (% of emitted dose <5 µm vs. emitted dose) is anticipated to be >15%.

Example 8

DPI Composition Containing 8'-OH Compound 154 g 8'-OH DHE mesylate is sandwich layered between a total of 847 g inhalation grade lactose (Respitose® SV003), and then is blended on a Turbula blender at 42 rpm for 45 minutes. The composition is then sieved through a 125 µm aperture sieve twice and filled (13 mg fill weight) into inhalation capsules. When tested for aerosol particle size distribution using a next generation Impactor (NGI) at 60 Lmin$^{-1}$, fine particles fraction (% of emitted dose <5 μm vs. emitted dose) is anticipated to be >15%.

Example 9

DPI Composition Containing 8'-OH Compound 77 g 8'-OH DHE mesylate is sandwich layered between a total of 423 g inhalation grade lactose (Respitose® ML001), and is then blended with high shear mixing at 2000 rpm for 45 minutes. The composition is then sieved through a 125 μm aperture sieve twice and filled (13 mg fill weight) into inhalation capsules. When tested for aerosol particle size distribution using a next generation Impactor (NGI) at 60 $Lmin^{-1}$, fine particles fraction (% of emitted dose <5 μm vs. emitted dose) is anticipated to be >15%.

Example 10

Nasal Suspension Composition Containing 8'-OH Compound

2% w/v 8'-OH DHE mesylate is suspended using high shear mixing into a composition comprising microcrystalline cellulose (Avicel RC-591, 1.5%), dextrose (5.0%), polysorbate 80 (0.007%), glycerol (4.0%), propylene glycol (1.0%), Citric acid monohydrate (0.2%), disodium hydrogen orthophosphate, anhydrous (0.31%), phenylethyl alcohol (0.275%), benzalkonium chloride (0.02%) and water (87.69%) and is filled into borosilicate glass bottles fitted with a pharmaceutically acceptable 100 μL metering valve. When tested using standard nasal testing equipment, shot weight is with 80-120% of target and emitted dose from the spray actuator is >80%.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating, preventing or ameliorating one or more symptoms of a migraine disease, condition or disorder, said method comprising administering a therapeutically effective dose of an 8'-hydroxy-dihydroegotamine (8'-OH DHE) composition to a subject in need of migraine treatment.

2. The method of claim 1, wherein said treatment comprises a reduction in a migraine symptom.

3. The method of claim 1, wherein said treatment comprises provision of partial relief from at least one migraine symptom.

4. The method of claim 3, wherein said treatment further comprises provision of sustained relief from one or more migraine symptom.

5. The method of claim 1, wherein said treatment is further characterized by not inducing one or more drug-induced side-effect.

6. The method of claim 5, wherein said treatment is further characterized by not inducing one or more drug-induced side-effect selected from nausea, emesis, chest tightness, and cardiovascular effects.

7. The method of claim 1, wherein said 8'-OH DHE composition is administered at a rate sufficient to provide a maximum circulating plasma level ($C_{max}$) of 8'-OH DHE that is less than 500 pg/mL.

8. The method of claim 1, wherein said 8'-OH DHE composition is administered at a rate sufficient to provide a maximum circulating plasma level ($C_{max}$) of 8'-OH DHE that is less than 2,500 pg/mL.

9. The method of claim 1, wherein said 8'-OH DHE composition is administered at a rate sufficient to provide a maximum circulating plasma level ($C_{max}$) of 8'-OH DHE that is less than 5,000 pg/mL.

10. The method of claim 1, wherein said 8'-OH DHE composition is administered in the form of a solution, suspension, tablet, dispersible tablet, pill, capsule, powder, sustained release composition, an elixir, a sterile solution or suspension suitable for parenteral administration, a topical dosage form, a transdermal dosage form, a nasal dosage form, or a pulmonary dosage form suitable for inhalation administration.

11. The method of claim 1, wherein said 8'-OH DHE composition is administered using a nebulizer, a DPI device, a MDI device, or a pMDI device.

* * * * *